US005658951A

United States Patent [19]
Magarian et al.

[11] Patent Number: 5,658,951
[45] Date of Patent: Aug. 19, 1997

[54] DIPHENYLCYCLOPROPYL ANALOGS

[75] Inventors: Robert A. Magarian; Joseph T. Pento; Lynette Overacre, all of Norman, Okla.

[73] Assignee: Research Corporation Technologies, Tucson, Ariz.

[21] Appl. No.: 487,717

[22] Filed: Jun. 7, 1995

Related U.S. Application Data

[63] Continuation-in-part of Ser. No. 376,961, Jan. 20, 1995, which is a continuation of Ser. No. 20,922, Feb. 22, 1993, Pat. No. 5,397,802, which is a continuation-in-part of Ser. No. 812,246, Dec. 19, 1991, abandoned, which is a continuation-in-part of Ser. No. 432,564, Nov. 6, 1989, Pat. No. 5,098,903, which is a continuation-in-part of Ser. No. 98,945, Sep. 21, 1987, Pat. No. 4,879,315, which is a continuation-in-part of Ser. No. 363,429, Mar. 30, 1982, abandoned, which is a continuation-in-part of Ser. No. 166,255, Jul. 7, 1980, abandoned, which is a continuation-in-part of Ser. No. 128,040, Mar. 7, 1980, abandoned.

[51] Int. Cl.$^6$ .......... A61K 31/135; A61K 31/10; C07C 301/00; C07C 43/20

[52] U.S. Cl. .......... 514/596; 514/651; 514/709; 514/710; 514/711; 514/717; 514/736; 558/44; 558/51; 558/53; 564/306; 568/583; 568/629; 568/647; 568/655; 568/774; 568/775; 568/807

[58] Field of Search .......... 514/596, 717, 514/709, 710, 711, 736, 651; 568/655, 629, 583, 647, 774, 775, 807; 558/44, 51, 53; 564/306

[56] References Cited

U.S. PATENT DOCUMENTS

| | | | |
|---|---|---|---|
| 4,442,119 | 4/1984 | Magarian et al. | 424/274 |
| 4,879,315 | 11/1989 | Magarian et al. | 514/754 |
| 5,015,666 | 5/1991 | Magarian et al. | 514/754 |
| 5,098,903 | 3/1992 | Magarian et al. | 514/255 |
| 5,324,736 | 6/1994 | Magarian et al. | 514/317 |
| 5,397,802 | 3/1995 | Magarian et al. | 514/546 |
| 5,422,367 | 6/1995 | Magarian et al. | 514/517 |

OTHER PUBLICATIONS

Day et al., "Synthesis and Biological Evaluation of a Series of 1, 1–dichloro–2,2,3–triarylcyclopropanes as Pure Antiestrogens", *Journal of Medicinal chemistry*, 1991, vol. 34, No. 2, pp. 842–851.

*Primary Examiner*—Marianne M. Cintins
*Assistant Examiner*—Dwayne C. Jones
*Attorney, Agent, or Firm*—Dunlap & Codding, P.C.

[57] ABSTRACT

Diphenylcyclopropyl analogs in which one or more of the phenyl rings includes alkoxy substituents including a dialkylaminoalkoxy group, an unsubstituted piperazine alkoxy group, a substituted piperazine alkoxy group, an unsubstituted piperidine alkoxy group, and a substituted piperidine alkoxy group, and which may have one or two alkyl groups bonded to the cyclopropane. The compounds are useful as antiestrogens and anti-tumor agents.

88 Claims, 9 Drawing Sheets

DIPHENYLCYCLOPROPYL ANALOGS

CROSS REFERENCE TO RELATED APPLICATIONS

This application is a continuation-in-part of U.S. Ser. No. 08/376,961, filed Jan. 20, 1995, entitled "GEM-DICHLORO-CYCLOPROPANES AS ANTITUMOR AGENTS.", which is a continuation of U.S. Ser. No. 08/020,922, filed Feb. 22, 1993, entitled "GEM-DICHLOROCYCLOPROPANES AS ANTITUMOR AGENTS", now U.S. Pat. No. 5,397,802, issued on Mar. 14, 1995, which is a continuation-in-part of U.S. Ser. No. 07/812,246, filed on Dec. 19, 1991, entitled "DIPHENYL-CYCLOPROPYL ANALOGS AS ANTIESTROGENIC AND ANTITUMOR AGENTS", now abandoned, which is a continuation-in-part of U.S. Ser. No. 07/432,564, filed Nov. 6, 1989, entitled "DIPHENYLCYCLOPROPANE ANALOGS AS ANTIESTROGENIC AND ANTITUMOR AGENTS", now U.S. Pat. No. 5,098,903, issued on Mar. 24, 1992, which is a continuation-in-part of U.S. Ser. No. 07/098,945, filed Sep. 21, 1987, entitled "CYCLOPROPYL ANALOGS AS ANTIESTROGENIC, ANTITUMOR AND FEMALE FERTILITY AGENTS", now U.S. Pat. No. 4,879,315, issued on Nov. 7, 1989, which is a continuation-in-part of U.S. Ser. No. 06/363,429, filed Mar. 30, 1982, entitled "CYCLOPROPYL ANALOGS AS ANTIESTROGENIC AND FEMALE FERTILITY AGENTS", now abandoned, which is a continuation-in-part of U.S. Ser. No. 06/166,255, filed Jul. 7, 1980, entitled "ANTIESTROGENIC CYCLOPROPYL ANALOGS AS ANTITUMOR AND FEMALE FERTILITY AGENTS", now abandoned, which is a continuation-in-part of U.S. Ser. No. 06/128,040, filed Mar. 7, 1980, entitled "ANTIESTROGENIC CYCLOPROPYL ANALOGS AS ANTITUMOR AND FEMALE FERTILITY AGENTS", now abandoned. U.S. Ser. No. 07/410,938, filed Sep. 22, 1989, entitled "TRIARYLCYCLOPROPANES AS ANTIESTROGENS AND ANTITUMOR AGENTS", now U.S. Pat. No. 5,015,666; U.S. Ser. No. 08/107,426, filed Aug. 16, 1993, now U.S. Pat. No. 5,324,736; and U.S. Ser. No. 08/201,737, filed Feb. 25, 1994, now U.S. Pat. No. 5,422,367, disclose related subject matter.

All applications cited above are hereby incorporated herein by reference in their entirety.

GOVERNMENTAL SUPPORT FOR INVENTION

This invention was made with Government support under a grant from the National Cancer Institute (CA40458). The Government has certain rights in this invention.

FIELD OF INVENTION

This invention relates to diphenylcyclopropyl analog compounds and their use in mammals for producing antiestrogenic activity in the mammal, and for inhibiting the development of an estrogen-dependent tumor in the mammal.

SUMMARY OF THE INVENTION

The present invention contemplates a compound having the formula:

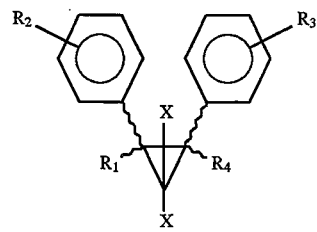

or any pharmaceutically acceptable salt thereof, in which:

X is a hydrogen or halogen atom;

$R_1$ is a hydrogen atom or an alkyl group containing from 1 to 3 carbon atoms;

$R_2$ is selected from the group consisting of,
a hydrogen atom, and
a substituted alkoxy group in which the substituent of the alkoxy group is selected from a group consisting of,
a dialkylamino group in which the alkyl substituent contains from 1 to 6 carbon atoms,
an alkylsulfonyloxy group in which the alkyl substituent contains from 1 to 6 carbon atoms,
an unsubstituted piperazine and a substituted piperazine in which the substituent is an alkyl group containing from 1 to six carbon atoms, and
an unsubstituted piperidine and a substituted piperidine in which the substituent is an alkyl group containing from 1 to six carbon atoms;

$R_3$ is selected from the group consisting of,
a hydrogen atom, and
a substituted alkoxy group in which the substituent of the alkoxy group is selected from a group consisting of,
a dialkylamino group in which the alkyl substituent contains from 1 to 6 carbon atoms,
an alkylsulfonyloxy group in which the alkyl substituent contains from 1 to 6 carbon atoms,
an unsubstituted piperazine and a substituted piperazine in which the substituent is an alkyl group containing from 1 to six carbon atoms, and
an unsubstituted piperidine and a substituted piperidine in which the substituent is an alkyl group containing from 1 to six carbon atoms; and $R_4$ is a hydrogen atom or an alkyl group containing from 1 to 3 carbon atoms; and with the proviso that $R_1$ and $R_4$ cannot simultaneously be hydrogen, and further with the proviso that $R_2$ and $R_3$ cannot simultaneously be hydrogen, and wherein the bonds designated by ($\sim$)

represent that the compound can be in the cis- or trans-isomer configuration.

The alkyl group in the $R_1$ and $R_4$ position may be methyl, ethyl or propyl. In a particularly preferred version, at least one of $R_1$ and $R_4$ is a methyl group and the compound is in the cis-configuration.

The compounds of the present invention may be combined with a pharmaceutically acceptable carrier to form pharmaceutical compositions.

The present invention further comprises a method of inducing antiestrogenic activity in a mammal in need of such therapy comprising administering to the mammal an antiestrogenically effective amount of one or more compounds having the above-described formula.

The present invention also comprises a method of inhibiting the development of an estrogen-dependent tumor in a mammal in need of such therapy comprising administering to the mammal an effective amount of one or more compounds having the above-described formula.

Another object of the present invention is to provide an improved antitumor agent which can be administered to a subject having an estrogen-dependent tumor to arrest the growth and development of the tumor while preventing metastatic involvement of such a tumor in the subject.

Another object of the present invention is to provide improved antitumor agents which do not possess estrogenic properties.

These and other objects, advantages and features of the present invention will be apparent to those skilled in the art from a reading of the following detailed description when read in conjunction with the drawings which accompany this disclosure and with the appended claims.

DETAILED DESCRIPTION OF THE INVENTION

Figure 1A:
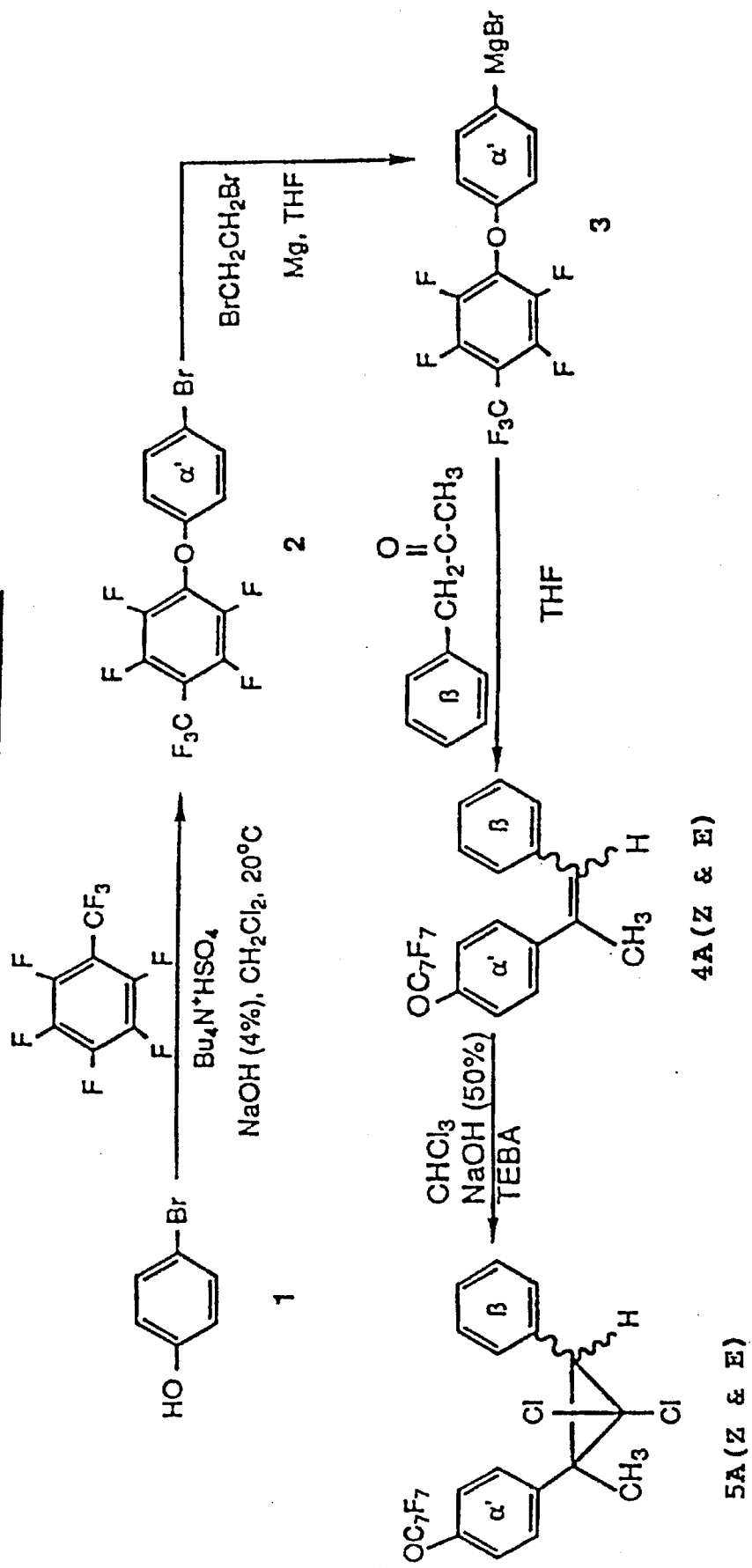
FIG. 1A is a portion of a scheme (Scheme I) showing a process for synthesizing four 2-methyl diphenylcyclopropanes, each having a different side chain.

The present invention contemplates a compound having the formula:

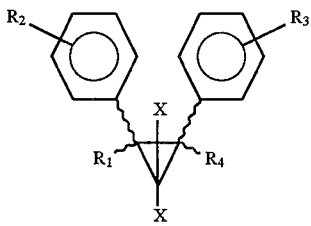

or any pharmaceutically acceptable salt thereof, in which:
X is a hydrogen or halogen atom;
$R_1$ is a hydrogen atom or an alkyl group containing from 1 to 3 carbon atoms;
$R_2$ is selected from the group consisting of,
  a hydrogen atom, and
  a substituted alkoxy group in which the substituent of the alkoxy group is selected from a group consisting of,
    a dialkylamino group in which the alkyl substituent contains from 1 to 6 carbon atoms,
    an alkylsulfonyloxy group in which the alkyl substituent contains from 1 to 6 carbon atoms,
    an unsubstituted piperazine and a substituted piperazine in which the substituent is an alkyl group containing from 1 to six carbon atoms, and
    an unsubstituted piperidine and a substituted piperidine in which the substituent is an alkyl group containing from 1 to six carbon atoms;
$R_3$ is selected from the group consisting of,
  a hydrogen atom, and
  a substituted alkoxy group in which the substituent of the alkoxy group is selected from a group consisting of,
    a dialkylamino group in which the alkyl substituent contains from 1 to 6 carbon atoms,
    an alkylsulfonyloxy group in which the alkyl substituent contains from 1 to 6 carbon atoms,
    an unsubstituted piperazine and a substituted piperazine in which the substituent is an alkyl group containing from 1 to six carbon atoms, and
    an unsubstituted piperidine and a substituted piperidine in which the substituent is an alkyl group containing from 1 to six carbon atoms; and
$R_4$ is a hydrogen atom or an alkyl group containing from 1 to 3 carbon atoms; and
with the proviso that $R_1$ and $R_4$ cannot simultaneously be hydrogen, and further with the proviso that $R_2$ and $R_3$ cannot simultaneously be hydrogen, and
wherein the bonds designated by ($\sim$)

represent that the compound can be in the cis- or trans-isomer configuration.

In a particularly preferred version, at least one of $R_1$ and $R_4$ is a methyl group and the compound is in the cis-configuration. The $R_2$ and $R_3$ groups may be at any position on the respective phenyl group, however, the para positions are preferred.

The present invention further contemplates a composition of matter comprising:
a compound having the formula:

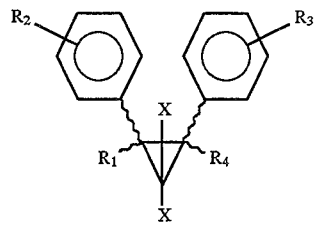

or any pharmaceutically acceptable salt thereof, in which:
X is a hydrogen or halogen atom;
$R_1$ is a hydrogen atom or an alkyl-group containing from 1 to 3 carbon atoms;
$R_2$ is selected from the group consisting of,
  a hydrogen atom, and
  a substituted alkoxy group in which the substituent of the alkoxy group is selected from a group consisting of,
    a dialkylamino group in which the alkyl substituent contains from 1 to 6 carbon atoms,
    an alkylsulfonyloxy group in which the alkyl substituent contains from 1 to 6 carbon atoms, an unsubstituted piperazine and a substituted piperazine in which the substituent is an alkyl group containing from 1 to six carbon atoms, and an unsubstituted piperidine and a substituted piperidine in which the substituent is an alkyl group containing from 1 to six carbon atoms;

$R_3$ is selected from the group consisting of,
a hydrogen atom, and
a substituted alkoxy group in which the substituent of the alkoxy group is selected from a group consisting of,
a dialkylamino group in which the alkyl substituent contains from 1 to 6 carbon atoms,
an alkylsulfonyloxy group in which the alkyl substituent contains from 1 to 6 carbon atoms,
an unsubstituted piperazine and a substituted piperazine in which the substituent is an alkyl group containing from 1 to six carbon atoms, and
an unsubstituted piperidine and a substituted piperidine in which the substituent is an alkyl group containing from 1 to six carbon atoms; and $R_4$ is a hydrogen atom or an alkyl group containing from 1 to 3 carbon atoms; and with the proviso that $R_1$ and $R_4$ cannot simultaneously be hydrogen, and further with the proviso that $R_2$ and $R_3$ cannot simultaneously be hydrogen, and wherein the bonds designated by ($\sim$)

represent that the compound can be in the cis-or trans-isomer configuration; and a pharmaceutically acceptable carrier of sufficient quantity to solubilize the compound.

In a particularly preferred version, at least one of $R_1$ and $R_4$ is a methyl group and the compound is in the cis-configuration.

The invention further contemplates a method of inducing antiestrogenic activity in a mammal in need of such therapy, comprising:

administering to the mammal an antiestrogenically effective amount of one or more of the compounds having the formula:

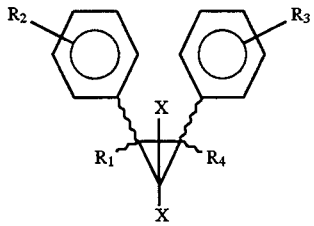

or any pharmaceutically acceptable salt thereof, in which:
X is a hydrogen or halogen atom;
$R_1$ is a hydrogen atom or an alkyl group containing from 1 to 3 carbon atoms;
$R_2$ is selected from the group consisting of,
a hydrogen atom, and
a substituted alkoxy group in which the substituent of the alkoxy group is selected from a group consisting of,
a dialkylamino group in which the alkyl substituent contains from 1 to 6 carbon atoms, an alkylsulfonyloxy group in which the alkyl substituent contains from 1 to 6 carbon atoms,
an unsubstituted piperazine and a substituted piperazine in which the substituent is an alkyl group containing from 1 to six carbon atoms, and
an unsubstituted piperidine and a substituted piperidine in which the substituent is an alkyl group containing from 1 to six carbon atoms;

$R_3$ is selected from the group consisting of,
a hydrogen atom, and
a substituted alkoxy group in which the substituent of the alkoxy group is selected from a group consisting of,
a dialkylamino group in which the alkyl substituent contains from 1 to 6 carbon atoms,
an alkylsulfonyloxy group in which the alkyl substituent contains from 1 to 6 carbon atoms,
an unsubstituted piperazine and a substituted piperazine in which the substituent is an alkyl group containing from 1 to six carbon atoms, and
an unsubstituted piperidine and a substituted piperidine in which the substituent is an alkyl group containing from 1 to six carbon atoms; and $R_4$ is a hydrogen atom or an alkyl group containing from 1 to 3 carbon atoms; and with the proviso that $R_1$ and $R_4$ cannot simultaneously be hydrogen, and further with the proviso that $R_2$ and $R_3$ cannot simultaneously be hydrogen, and wherein the bonds designated by ($\sim$)

represent that the compound can be in the cis-or trans-isomer configuration.

In a particularly preferred version, at least one of $R_1$ and $R_4$ is a methyl group and the compound is in the cis-configuration.

The present invention further contemplates a method of inhibiting the development of an estrogen-dependent tumor in a mammal in need of such therapy, comprising: administering to the mammal an effective amount of one or more of the compounds having the formula:

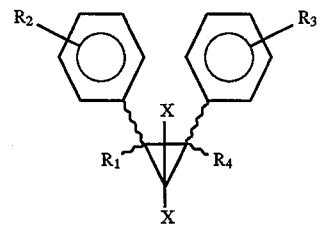

or any pharmaceutically acceptable salt thereof, in which:
X is a hydrogen or halogen atom;
$R_1$ is a hydrogen atom or an alkyl group containing from 1 to 3 carbon atoms;
$R_2$ is selected from the group consisting of, a hydrogen atom, and
a substituted alkoxy group in which the substituent of the alkoxy group is selected from a group consisting of,
a dialkylamino group in which the alkyl substituent contains from 1 to 6 carbon atoms,
an alkylsulfonyloxy group in which the alkyl substituent contains from 1 to 6 carbon atoms,
an unsubstituted piperazine and a substituted piperazine in which the substituent is an alkyl group containing from 1 to six carbon atoms, and an unsubstituted piperidine and a substituted piperidine in which the substituent is an alkyl group containing from 1 to six carbon atoms;

$R_3$ is selected from the group consisting of,
a hydrogen atom, and
a substituted alkoxy group in which the substituent of the alkoxy group is selected from a group consisting of,
a dialkylamino group in which the alkyl substituent contains from 1 to 6 carbon atoms,
an alkylsulfonyloxy group in which the alkyl substituent contains from 1 to 6 carbon atoms,
an unsubstituted piperazine and a substituted piperazine in which the substituent is an alkyl group containing from 1 to six carbon atoms, and
an unsubstituted piperidine and a substituted piperidine in which the substituent is an alkyl group containing from 1 to six carbon atoms; and $R_4$ is a hydrogen atom or an alkyl group containing from 1 to 3 carbon atoms; and with the proviso that $R_1$ and $R_4$ cannot simultaneously be hydrogen, and further with the proviso that $R_2$ and $R_3$ cannot simultaneously be hydrogen, and wherein the bonds designated by (∼)

represent that the compound can be in the cis-or trans-isomer configuration.

In a particularly preferred version, at least one of $R_1$ and $R_4$ is a methyl group and the compound is in the cis-configuration.

In the compounds of the present invention any of the foregoing groups described herein as being represented by $R_2$ may also be at the $R_3$ position provided that both $R_2$ and $R_1$ may not both be simultaneously hydrogen.

When the compound of the present invention is optically active, each optical isomer thereof, as well as racemic mixtures thereof of optical isomers having the same chemical structures are within the scope of the present invention.

In particularly preferred versions, the present invention comprises the above compound with (1) a methyl group in the 2 position of the cyclopropane, (2) a methyl group in the 3 position of the cyclopropane, or (3) methyl groups in both the 2 and 3 positions of the cyclopropane. It is now known that basic side chains (e.g., dimethylaminoethoxy) in antiestrogen/antitumor agents are responsible for their biological action. The strategic addition of other groups, such as alkyl groups as described herein, can lead to enhanced antiestrogenic/antitumor activity due to increased lipid solubility resulting in increased biological half-life.

A preferred compound contemplated herein is a diphenylcyclopropane in the cis-isomer configuration wherein either $R_2$ or $R_3$ comprises a dimethylaminoethoxy side chain such as represented below and including each of its (R) and (S) optical isomers and racemic mixtures thereof:

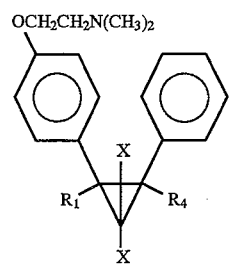

In another preferred embodiment, the present invention comprises modified versions of the above compound comprising (1) a methyl group in the 2 position of the cyclopropane, (2) a methyl group in the 3 position of the cyclopropane, or (3) methyl groups in both the 2 and 3 positions of the cyclopropane. These three Versions, wherein X comprises chlorine, are indicated below:

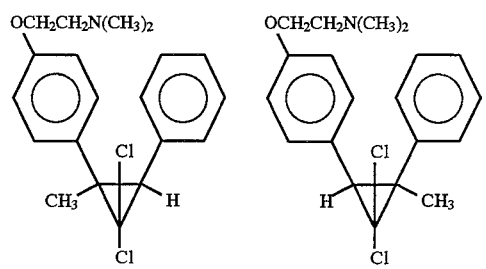

Another preferred compound contemplated herein is a diphenylcyclopropane in the cis-isomer configuration wherein either $R_2$ or $R_3$ comprises a diethylaminoethoxy side chain such as represented below and including each of its (R) and (S) optical isomers and racemic mixtures thereof:

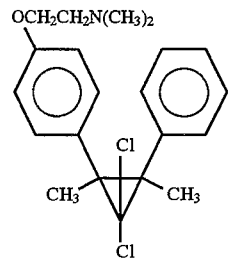

In another preferred embodiment, the present invention comprises modified versions of the above compound comprising (1) a methyl group in the 2 position of the cyclopropane, (2) a methyl group in the 3 position of the cyclopropane, or (3) methyl groups in both the 2 and 3 positions of the cyclopropane. These three versions, wherein X comprises chlorine, are indicated below:

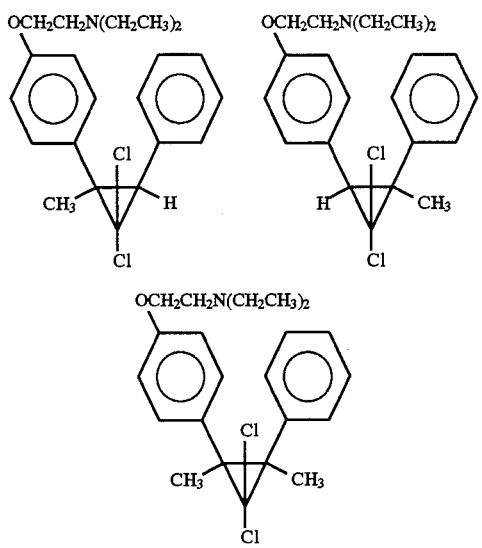

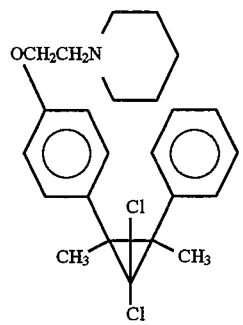

Another preferred compound contemplated herein is a diphenylcyclopropane in the cis-isomer configuration wherein either $R_2$ or $R_3$ comprises a piperidinoethoxy side chain such as represented below and including each of its (R) and (S) optical isomers and racemic mixtures thereof:

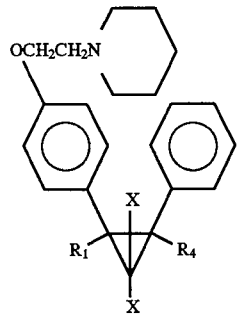

In another preferred embodiment, the present invention comprises modified versions of the above compound comprising (1) a methyl group in the 2 position of the cyclopropane, (2) a methyl group in the 3 position of the cyclopropane, or (3) methyl groups in both the 2 and 3 positions of the cyclopropane. These three versions, wherein X comprises chlorine, are indicated below:

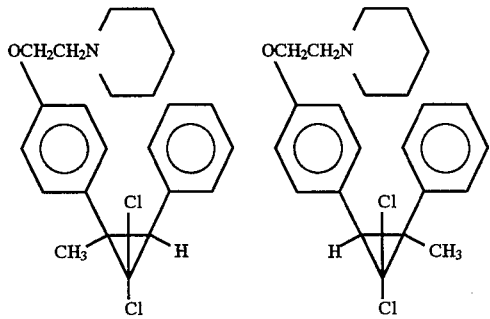

Another preferred compound contemplated herein is a diphenylcyclopropane in the cis-isomer configuration wherein either $R_2$ or $R_3$ comprises a methylpiperazinoethoxy side chain such as represented below and including each of its (R) and (S) optical isomers and racemic mixtures thereof:

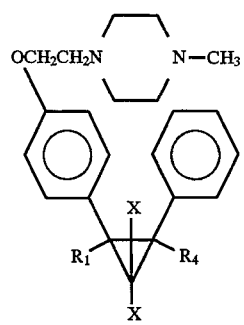

In another preferred embodiment, the present invention comprises modified versions of the above compound comprising (1) a methyl group in the 2 position of the cyclopropane, (2) a methyl group in the 3 position of the cyclopropane, or (3) methyl groups in both the 2 and 3 positions of the cyclopropane. These three versions, wherein X comprises chlorine, are indicated below:

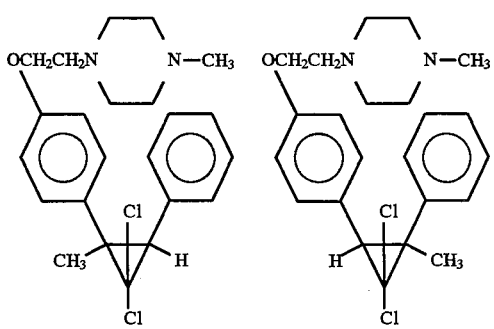

-continued

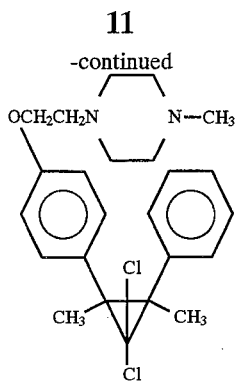

Preferably, the compounds of the present invention are combined with a pharmaceutically acceptable carrier to form a pharmaceutical composition appropriate for therapeutic delivery to a mammal. The pharmaceutically acceptable carrier should not substantially interfere with the antiestrogenic and anti-tumor activities of the compound, and may be a solid or liquid in which the compound is solubilized, suspended or dispersed in any manner.

The cyclopropyl analogs used in accordance with the present invention are generally solid materials. Thus, it may be desirable to suspend, emulsify, solubilize, or disperse the antiestrogenic cyclopropyl analog in a suitable vehicle to facilitate the administration of the antitumor agent to the subject. In such instance, any suitable vehicle can be employed provided the vehicle is inert to the antiestrogenic cyclopropyl analog and to the subject. Such vehicles and the methods for suspending, emulsifying, solubilizing, or dispersing the antiestrogenic cyclopropyl analogs in a suitable vehicle are well known in the art of pharmaceutical formulations and thus a further description of same is not believed necessary herein.

The compounds of the present invention may be administered orally in solid dosage forms, such as tablets and powders, or in liquid dosage forms, such as elixirs, syrups and suspensions; they may also be administered parenterally, in sterile liquid dosage forms. Such parenteral administration may include intravenous, intramuscular, subcutaneous, intra-arterial, and direct tumor perfusion techniques.

If the compound is to be injected, the pharmaceutical carrier should preferably be isotonic, and have about a physiological pH. Suitable pharmaceutical carriers for parenteral administration may be any suitable oil, saline, aqueous dextrose or related sugar solutions, or glycols such as propylene glycol or polyethylene glycols. Solutions for parenteral administration contain preferably a water soluble salt of the active ingredient, suitable stabilizing agents, and if necessary, buffer substances. Additionally, parenteral solutions can contain preservatives. Other suitable pharmaceutical carriers are described in *Remington's Pharmaceutical Sciences*, Mack Publishing Co., and similar reference texts.

The present invention further comprises a method of inducing antiestrogenic activity in a mammal, such as a human, in need of such therapy comprising administering to the mammal an antiestrogenically effective amount of one or more compounds having the formula, preferably in the form described above. The dosage of the compounds of the present invention may vary due to the therapeutically desired result which is affected by the type of disease or condition in the mammal; the age, weight and health of the recipient; the severity of the condition or disease in the mammal; the kind of concurrent treatment, if any, being administered to the mammal; and the frequency of treatment. Generally, a therapeutically effective dosage is less than about 0.5 mg to about 2 mg per kilogram of bodyweight of the mammal over a 24 hour period. The method of administration of the compound of the present invention can be any suitable method as previously described.

The present invention also comprises a method of inhibiting the development of an estrogen-dependent tumor in a mammal, such as a human, in need of such therapy comprising administering to the mammal a therapeutically effective amount of one or more compounds having the formula described above, preferably in the form of a pharmaceutical composition comprising at least one of the compounds combined with a pharmaceutically acceptable carrier. "Inhibiting the development of an estrogen-dependent tumor" means either slowing the growth of a tumor, diminishing the size of a tumor, or preventing the formation of a tumor from cells having the potential of developing into a tumor wherein the tumor requires the presence of an estrogenic substance for the growth, development and/or metastatic involvement of the tumor.

The compounds previously described may be administered to the mammal to inhibit the development of the estrogen-dependent tumor by an administration method of the type previously described. The dosage may vary according to the type of the disease; the size of the tumor or tumors, if present; and the quantity of tumors as well as other factors previously described. Generally, a daily dosage of less than about 0.5 mg to about 2 mg/kg of body weight of the mammal will suffice.

The following examples are given to illustrate the effectiveness of the before-defined anti-estrogenic cyclopropyl analogs in substantially preventing or arresting the growth, development and metastatic involvement of estrogen-dependent tumors. The examples are for illustrative purposes only and are not to be construed as unduly limiting the scope of the invention as hereinafter recited in the claims. All parts and percentages in the examples, unless otherwise specified, are parts by weight and weight percentages.

EXAMPLE 1

A series of cyclopropyl analogs were prepared using several procedures. The gem-dichlorocyclopropyl analogs were prepared by either procedure A or B. The reduced analogs (i.e., the analogs without gem-dichlorocyclopropyl groups) were prepared using either the Procedure A or B in combination with Procedure C. It should be noted, however, that in those instances where it was desired that the analog contain a hydroxyl moiety on the phenyl ring, such as in the para position, Procedure A was followed.

In each of the following Procedures A and B, 1,1-dichloro-cis-2,3-diphenylcyclopropane was prepared as an illustrative example of the cyclopropyl analogs for use in the practice of the present invention. When the gem-dichlorocyclopropanes so prepared were reduced to remove the chlorine atoms, such reductions were carried out using sodium metal in wet methanol. Procedure C is illustrative of the before-mentioned reductive procedure in which cis-1,2-diphenylcyclopropane was prepared.

Procedure A—Preparation of gem-dichlorocyclopropyl analogs 3.6 g (0.02 mole) or cis-stilbene was added to 10.0 g (0.002 mole) or phenyl(bromodichloromethyl)mercury in benzene. After the resulting solution was refluxed with stirring under dry nitrogen and maintained at 82°–88° C. in an oil bath for 1.5 hour with stirring, phenylmercuric bromide precipitated (7.2 g, 92%) and the reaction mixture turned yellow. The relative proton absorption in the NMR spectrum showed small quantities of the unchanged olefin.

The mixture then was refluxed with stirring for an additional hour. The NMR spectrum of this mixture indicated that the olefin had reacted. Benzene was removed on a flash evaporator, yielding 6.5 g of crude product, which was dissolved in petroleum ether (bp 30°–60° C.) and filtered to remove a small amount of white precipitate, mp 175° C. The crude product was purified through a 2×18 cm column of neutral alumina (activity I) using purified petroleum ether (bp 30°–60° C). A cream-colored oil was eluted, which solidified after standing in a refrigerator overnight. The solid had a melting point range of 49°–51° C. and weighed 4.5 g (86%).

An analytical sample was obtained by sublimation. The sublimator was kept in 45° C. (0.03 mm) in an oil bath while the inner cold finger was maintained at −5° C. by cold water pump. The white needles melted at 50°–51.5° C. NMR and infrared spectra verified the product of 1,1-dichloro-cis-2, 3-diphenylcyclopropane.

Procedure B—Preparation of gem-dichlorocyclopropyl analogs

To a cold solution of 0.50 g (0.002 mole) of triethylbenzylammonium chloride and 110 ml of chloroform in a three-necked flask was added 6.0 g (0.33 mole) of cis-stilbene, and the solution was stirred to dissolve the stilbene. A 50% sodium hydroxide solution (75 g) was added carefully through a dropping funnel; it was stirred at 10°–20° C. for 6 hours and then at room temperature for 24 hours by means of a magnetic stirrer. The mixture was diluted with 100 ml of water, and a dark-brown chloroform layer separated. The aqueous phase was extracted with three 50 ml portions of methylene chloride, and the organic layers were collected and dried over anhydrous magnesium sulfate. Evaporation of the solvent in vacuo yielded 7.5 g of dark-brown oil.

The crude oil was purified by placing it on a 1.3×33 cm column of alumina (activity I) and eluting with purified petroleum ether (bp 30°–60° C). A cream-colored oil, 6.0 g (69%), solidified at 0° C., and had amp 48°–49° C.

The Ir and NMR spectra of the product were identical to those of the product obtained using Procedure A.

Procedure C—Reduction of gem-dichlorocyclopropyl analogs to remove the chloro groups A solution of 2.0 g (0.008 mole) of 1,1-dichloro-cis-2,3-diphenylcyclopropane and 30 ml of ether in a 250 ml three-necked flask, fitted with a dry ice-acetone condenser, was stirred (magnetic stirrer) in an ice water bath. Sodium metal (6.9 g; 0.3 g-atom) was added in small pieces over 1.5 hour, and 60 ml of wet methanol (2 ml of water) was introduced slowly through a dropping funnel with stirring (magnetic stirrer). After all of the sodium metal reacted, 20 ml of water was added and the aqueous layer was extracted with two 30 ml portions of ether.

The aqueous phase was neutralized slowly with concentrated hydrochloric acid on an ice-salt bath and extracted with two 30 ml portions of ether. The ether extracts were dried over anhydrous magnesium sulfate and filtered. Evaporation of ether at 30° C. under vacuum yielded 1.5 g of yellow oil, which solidified when left at 0° C. Sublimation at 40°–50° C. (0.04–0.05 mm) with the cold finger at −40° C. yielded 1.0 g (68%) of white needles, mp 38°–38.5° C. NMR and Infrared spectra verified the production of cis-1, 2-diphenylcyclopropane. The cyclopropyl analogs so prepared and utilized in the following test procedures are tabulated as follows:

TABLE I

| CYCLOPROPYL ANALOGS | |
|---|---|
| Analog No. | Chemical Name |
| I | 1,1-Dichloro-trans-2,3-diphenylcyclopropane |
| II | 1,1-Dichloro-cis-2,3-diphenylcyclopropane |
| III | Trans-1,2-Diethyl-1,2-(4,4'-dimethoxyphenyl)-cyclopropane |
| IV | 1,1-Dichloro-trans-2,3-diethyl-2,3-(4,4'-dihydroxyphenyl)cyclopropane |
| V | 1,1-Dichloro-trans-2,3-diethyl-2,3-(4,4'-diacetoxyphenyl)cyclopropane |
| VI | 1,1-Dichloro-trans-2,3-(4,4'-dimethoxyphenyl)-cyclopropane |
| VII | 1,1-Dichloro-trans-2,3-diethyl-2,3-(4,4'-dimethoxyphenyl)cyclopropane |
| VIII | Trans-1,2-Diethyl-1,2-(4,4,-dihydroxyphenyl)-cyclopropane |
| IX | Cis-1,2-Diphenylcyclopropane |
| X | Trans-1,2-Diphenylcyclopropane |

EXAMPLE 2

Procedure D—Preparation of 1,1-dichloro-cis-2-(p-methoxyphenyl)-3-phenylcyclopropane, 1,1-dichloro-cis-2-(p-hydroxy-phenyl)-3-phenylcyclopropane and 1,1-dichloro-cis-2-(p-acetoxyphenyl)-3-phenylcyclopropane A mixture of 27.23 g (0.20 mole) of 4-methoxybenzaldehyde and 27.23 g (0.20 mole) of phenyl acetic acid was added to a mixture of 20 ml of triethylamine and 40 ml of acetic anhydride. This solution was refluxed with stirring over 4–5 hours. The reaction mixture was cooled and 200 ml of 20% sodium hydroxide was added. Anhydrous diethyl ether was used to extract this mixture and the combined ethereal layers were discarded. The aqueous layer was acidified with concentrated hydrochloric acid resulting in a solid which was removed by filtration. Purification of the product was accomplished by recrystallization from aqueous ethanol which yielded 27.0 g (54%) of cis-α-phenyl-p-methoxy cinnamic acid in the form of light yellow needles.

A solution of 12.70 g (0.05 mole) of cis-α-phenyl-p-methoxy cinnamic acid in 64.5 g (0.50 mole) quinoline was stirred as 0.90 g of copper chromite was added. To achieve decarboxylation, the mixture was heated to 180° C. which releases carbon dioxide. The presence of quinoline prevents isomerization to the more stable trans configuration during the heating stage. The mixture was kept at 180°–190° C. for 1 ½ hours. The solution was transferred after cooling to a separatory funnel with 100 ml of anhydrous diethyl ether. Approximately 500 ml of 15% hydrochloric acid solution was used to extract the residual quinoline. The ether layer was filtered to remove particles of the catalyst, and washed with saturated sodium chloride solution. That layer was then dried with magnesium sulfate and concentrated by rotary vacuum evaporation. The brown residual oil was purified by vacuum distillation to yield 6.0 g (57%) of cis-p-methoxy stilbene.

A solution of 5.25 g (25 mMol) of cis-p-methoxy stilbene and 0.57 g (2.5 mMol) of triethylbenzyl ammonium chloride in 80 ml of chloroform was stirred while 60 g of 29% cold sodium hydroxide solution was added by drops. The solution was stirred for 20 hours. Layers were separated and the aqueous layer was extracted with three 50 ml portions of methylene chloride. The combined organic layers were washed with three 50 ml portions of saturated salt solution and dried over anhydrous magnesium sulfate. Filtration and concentration produced a dark brown oil which was heated with 30 ml of petroleum ether, and then was filtered to remove the insoluble residue. After the petroleum ether was evaporated, a small amount of ethanol was added and cooled at 0° C. to give a light brown solid. After recrystallization with ethanol, 1,1-dichloro-cis-2-(p-methoxyphenyl)-3-phenylcyclopropane was formed.

A solution comprising 3.0 ml of dry methylene chloride and 2.1 ml of n-Butanephiol was stirred under argon. To this solution was added 1.33 g (10 mMol) of aluminum chloride. Also added to this solution was 0.586 g (2 mMol) of 1,1-dichloro-cis-2-(p-methoxyphenyl)-3-phenylcyclopropane in 10 ml of dry methylene chloride by drops. The mixture was stirred at room temperature for 40 minutes and then cooled in an ice bath. Ice cold water was added by drops slowly to decompose the aluminum chloride. After the layers were separated, three 10 ml portions of anhydrous diethyl ether were used to extract the aqueous layer. The combined organic layers were dried with magnesium sulfate, filtered and concentrated to yield a brown oil (crude yield 90%). Unreacted n-Butanephiol and a by-product n-Butyl methyl sulfide were evaporated by connecting the crude product to a vacuum pump which yielded a light brown oil containing 1,1-dichloro-cis-2-(p-hydroxyphenyl)-3-phenylcyclopropane.

A solution of 10 ml of anhydrous diethyl ether, 10.0 mMol of crude product of 1,1-dichloro-cis-2-(p-hydroxyphenyl)-3-phenylcyclopropane and 0.79 g (10 mMol) of pyridine was heated to gentle refluxing. Acetyl chloride, 0.78 g (10 mMol), was added by drops very slowly, which immediately formed a white precipitate. The mixture continued to reflux gently for one hour after all the acetyl chloride was added. The reaction flask was cooled in an ice bath while 5.0 ml of water was added by drops. The aqueous layer was extracted by using three 10 ml portions of anhydrous diethyl ether. The combined ether layer was washed with three 10 ml portions of 5% sulfuric acid and saturated sodium bicarbonate solution. It was then dried with sodium sulfate and evaporated to give a dark yellow oil which was purified by column chromatography on silica gel with methylene chloride-petroleum ether (3:1) as eluent to yield a yellow oil containing 1,1-dichloro-cis-2-(p-acetoxyphenyl)-3-phenylcyclopropane Procedure E—Preparation of 1,1-dichloro-2,2-Bis-(p-methoxyphenyl)cyclopropane, 1,1-dichloro-2-(p-methoxyphenyl)-2-(p-hydroxyphenyl) cycloproane and 1,1-dichloro-2,2-Bis-p-hydroxy-phenyl) cyclopropane A Grignard reagent was prepared with 2.43 g (0.1 mole) of magnesium turning and 18.7 g (0.1 mole) p-bromoanisole in 20 ml of dry ether. It was refluxed for 30 minutes after most of the magnesium had dissolved. To this solution was added by drops 3.97 g (45 mMol) of ethyl acetate in 10 ml of dry ether over 30 minutes, and the reaction mixture was refluxed for one hour. The mixture was cooled to room temperature; 40 ml of 5N sulfuric acid and 40 ml of ether was added slowly. The mixture was stirred for a few hours and allowed to sit overnight. The layers were then separated and the aqueous layer was extracted with chloroform and then washed with a saturated salt solution, dried over anhydrous magnesium sulfate, and evaporated to give the alkene product as a light yellow solid. Recrystallization in ethanol yielded 4.0 g (37%) white flaky solid comprising 1,1-Bis-(p-methoxyphenyl) ethylene.

A solution of 4.8 g (20 mMol) of 1,1-Bis-(p-methoxyphenyl) ethylene and 0.46 g (2mMol) of triethyl-benzyl ammonium chloride in 80 ml of chloroform was stirred while 48 g of 29% cold sodium hydroxide solution (166 ml) was added by drops over 2 hours. This was stirred for 17 hours. Layers were separated and the aqueous layer was extracted with three 50 ml portions of methylene chloride. The combined organic layer was washed with three 50 ml portions of saturated salt solution and dried over anhydrous magnesium sulfate. Filtration and concentration yielded a yellow solid which was recrystallized in ethanol to give yellow needles. Further recrystallization with cyclohexane-ethanol (40:50) yielded 4.66 g (72%) yellow needles containing 1,1-dichloro-2,2-Bis-(p-methoxyphenyl) cyclopropane.

Placed in an oven-dried, three-necked flask was 1.615 g (5 mMol) of 1,1-dichloro-2,2-Bis-(p-methoxyphenyl) cyclopropane which was flushed with argon and sealed with a rubber septum. Using oven-dried syringes, 10 ml of chloroform, 0.32 g (4 mMol) of pyridine and 2.9 ml (20 mMol) of iodotrimethylsilane were injected into the flask in the order specified above (the chloroform and pyridine had been dried previously over anhydrous magnesium sulfate). The mixture turned yellow and a white precipitate was noted with the addition of iodotrimethylsilane. The mixture turned yellow and a white precipitate was noted with the addition of iodotrimethylsilane. The mixture was heated to reflux without stirring for 72 hours. Thin layer chromatography was performed with methylene chloride and a small amount of starting material still was present. Anhydrous methanol, dried with magnesium sulfate, in the amount of 2.5 ml was added and the mixture turned golden brown. It was cooled to room temperature and transferred to a round bottom flask with 10 ml of chloroform. The volatile components were removed on a rotary evaporator to yield a yellow solid which was dissolved in 50 ml of ether. The insoluble pyridium hydrochloride was filtered. The ether was evaporated to afford a yellow solid whose NMR and thin layer chromatography (with methylene chloride-acetone (95:5)) showed starting material along with some polar components. These components were separated by column chromatography on silica gel (125 g) with methylene chloride-acetone (95:5) as eluent. Unreacted starting material was eluted first and 0.4 g was recovered. Compound 1,1-dichloro-2-(p-methoxyphenyl)-2-(p-hydroxyphenyl) cyclopropane was eluted next and recrystallized in hexane with trace of ethanol to give colorless fine needles. The column was then washed with acetone, and compound 1,1-dichloro-2,2-Bis-(p-hydroxyphenyl) cyclopropane as a red brown solid was obtained upon evaporation of the solvent. This solid was recrystallized in chloroform to give a light pink solid.

Procedure F—Preparation of 1,1-dichloro-2,2-Bis-(p-methoxyphenyl)-3-phenylcyclopropane A solution of 6.9 g (30 mMol) of p-methoxy deoxybenzoin in 20 ml of benzene was prepared and 6.9 g (33 mMol) of phosphorus pentachloride added thereto. After stirring at room temperature for 15 hours the reaction was completed. This mixture was poured into 50 g crushed ice and 40 ml of ether was used to rinse out the flask. The layers were separated, and the aqueous layer was extracted with three 40 ml portions of ether. The combined ether layer was dried over anhydrous sodium sulfate. A reddish oil obtained Upon evaporation of the solvent solidified immediately. It was washed with methanol and recrystallized in ether to yield 5.1 g (70%) of p-methoxy-α'-chlorostilbene.

A solution was made from 4.8 g (20 mMol) of p-methoxy-α'-chlorostilbene and 2.6 g (24 mMol) of anisole in 12 ml of carbon disulfide. To this solution, 3.4 g (26 mMol) pulverized aluminum chloride was added slowly over 30 minutes. The mixture turned crimson red and was stirred at room temperature for 4 hours. About 40 g of crushed ice and 40 ml of ether was added and the reaction mixture turned to a yellowish color upon decomposition of the aluminum chloride. The layers were separated, and the aqueous layer was extracted with three 20 ml portions of ether. Combined ether layer was washed with two 25 ml portions of saturated salt solution (brine), and dried over anhydrous sodium sulfate. An orange oil obtained was dissolved in hot ethanol and cooled at 0° C. A yellow oil precipitated while the colorless supernatant was pipetted out carefully. A colorless solid was crystallized from this supernatant. Subsequent treatment of the yellow oil with ethanol yielded 4.55 g (72%) solid 1,1-Bis-(p-methoxy-phenyl)-2-phenylethylene.

A solution was prepared containing 4.74 g (15 mMol) of 1,1-Bis-(p-methoxyphenyl)-2-phenyl ethylene and 0.34 g (1.5 mMol) of triethylbenzyl ammonium chloride in 45 ml of chloroform. To this solution 34 g of 50% cold sodium hydroxide solution (69 ml) was added by drops through a dropping funnel. The mixture was stirred vigorously at room temperature for 8 hours, and diluted with 40 ml of water. A dark brown chloroform layer was separated, and the aqueous layer was extracted with three 25 ml portions of methylene chloride. The combined organic layer was washed over three 40 ml portions of saturated salt solution (brine), and dried over anhydrous magnesium sulfate. Evaporation of the solvent in vacuo yielded 6.6 g dark brown syrupy oil which was dissolved in hot hexane. Some insoluble brown crust was filtered and the hexane filtrate was cooled at 0° C. to yield a yellow solid which was recrystallized in cyclohexane-ethanol (60:40) to give light yellow crystals comprising 1,1-dichloro-2,2-Bis-(p-methoxyphenyl)-3-phenylcyclopropane.

Procedure G—Preparation of 1,1-dichloro-2,2-Bis-(p-methoxyphenyl)-spiro [2.5] octane A Grignard reagent was prepared with 1.94 g (80 mMol) of magnesium turning and 15.0 g (80 mMol) of p-bromoanisole in 40 ml of dry ether. Methyl cyclohexane carboxylate, 5.7 g (40 mMol), in 15 ml dry ether was added by drops over 20 minutes. After an hour of refluxing, the reaction mixture was poured into an acidic solution of 30 g of ice, 30 ml of water, and 6.0 ml of concentrated sulfuric acid for hydrolysis. The aqueous layer was then extracted with three 20 ml portions of ether. The combined ether layer was washed with two 50 ml portions of 10% sulfuric acid solution and dried over anhydrous sodium sulfate. Filtration and evaporation yielded an orange yellow oil which is shown to be Bis-(p-methoxyphenyl)-cyclohexyl methanol. The dehydration was accomplished by combining 3.0 ml of concentrated sulfuric acid in 10.0 ml of acetic acid and adding this solution slowly by drops to the Bis-(p-methoxyphenyl)-cyclohexyl methanol while it was cooled in an ice bath. The mixture turned dark red and solidified. A small amount of ether was added to facilitate the stirring. After 2 hours of stirring at room temperature, 20 ml of water and 20 ml of ether were added. The aqueous layer was extracted with three 15 ml portions of ether, and the combined ether layer was washed with two 25 ml portions of saturated salt solution (brine), and dried over anhydrous sodium sulfate. Upon evaporation of the solvent, the yellow solid obtained was recrystallized in ethanol. Further recrystallization affords 8.0 g (65%) colorless solid containing Bis-(p-methoxyphenyl)-cyclohexylidene methane.

A solution of 6.16 g (20 mMol) of Bis-(p-methoxyphenyl)-cyclohexylidene methane and 0.46 g (2 mMol) of triethylbenzyl ammonium chloride in 65 ml of chloroform was stirred while 48 g of 50% cold sodium hydroxide solution (96 ml) was added by drops. The mixture was stirred vigorously for 84 hours at room temperature. The layers were separated, and the aqueous layer was extracted with five 30 ml portions of methylene chloride. The combined organic layer was washed with five 50 ml portions of saturate salt solution (brine), and dried over anhydrous sodium sulfate. Filtration and evaporation afforded a dark brown thick oil which was dissolved in hot petroleum ether. Some insoluble brown crust was filtered as well as a yellow solid precipitate from the petroleum ether filtrate. Colorless fine needles were obtained from subsequent recrystallizations in cyclohexane containing 1,1-dichloro-2,2-Bis-(p-methoxyphenyl)-spiro [2.5] octane.

Procedure H—Preparation of 1,1-dichloro-cis-2,3-Bis-(p-methoxyphenyl) cyclopropane A solution of 5.68 g (20 mMol) of 2,3-Bis-(p-methoxyphenyl) acrylic acid in 10.0 ml of quinoline was stirred while 0.4 g of copper chromite was added. Carbon dioxide was released when the temperature of the reaction mixture reached 180° C. The solution was then cooled and 60 ml of ether was used to transfer the reaction mixture to a separatory funnel. Approximately 500 ml of 15% hydrochloric solution was used to extract the residual quinoline. The ether layer was filtered to remove particles of catalyst, and washed with saturated sodium chloride solution. It was then dried over anhydrous magnesium sulfate and concentrated to yield a dark brown oil. The trans-olefin in the amount of 0.07 g was collected when ethanol was used to attempt crystallization. Petroleum ether was used to dissolve the brown oil and cool at 0° C. to give the cis-isomer as flaky solid. Recrystallization yielded 2.81 g (58%) solid containing Bis-(p-methoxy)-cis-stilbene.

A solution of 6.46 g (27 mMol) of Bis-(p-methoxy)-cis-stilbene and 0.46 g (2.0 mMol) of triethylbenzyl ammonium chloride in 65 ml of chloroform was stirred while 40 g of 29% cold sodium chloride solution (138 ml) was added by drops. The vigorous stirring was continued for 17.5 hours. The layers were separated and the aqueous layer was extracted with three 50 ml portions of methylene chloride. The combined organic layer was washed with three 50 ml portions of saturated sodium chloride solution and dried over anhydrous magnesium sulfate. Filtration and concentration yielded a dark brown oil which was heated to dissolve in hexane. After some insoluble brown crust was filtered, the hexane filtrate was allowed to cool to give a yellow solid which was recrystallized in ethanol to yield 5.57 g (64%) light yellow fine needles containing 1,1-dichloro-cis-2,3-Bis-(p-methoxyphenyl) cyclopropane.

EXAMPLE 3

Procedure J—Biological Methods—Uterotropic Assay for Estrogenic and Anti-Estroqenic Activity The assay for estrogenic activity employed immature Swiss-Webster mice weighing 10–14 g (approximately 21 days old). The animals were randomly distributed into groups containing 5–6 mice each. Estradiol and the test compounds were dissolved separately in sesame oil and administered subcutaneously in a volume of 0.1 ml. Control animals were treated with the same volume of sesame oil alone.

All animals were treated daily for three consecutive days. O n the fourth day the animals were sacrificed and the uteri carefully dissected, blotted lightly and weighed to the nearest 0.1 mg. Body weights were also recorded. Estradiol was used in a dosage range of 0.01–0.04 ug (total dose) as the assay standard. Each cyclopropyl analog was examined over a dosage range of 1–25 ug (total dose).

The uterotropic assay was also used to evaluate the anti-estrogenic activity of the test compounds which did not produce an estrogenic response in the previous assay. The anti-estrogenic assay was conducted as described above for estrogenic activity except that each animal in the cyclopropyl analog treatment groups received a standard stimulating dose of estradiol (0.0.4 ug). The test compounds and estradiol were administered separately at different injection sites to minimize possible physical interaction or reduced absorption of either compound. Anti-estrogenic activity was measured as a decrease in estradiol-stimulated uterotropic response in groups which received both the test compound and estradiol as compared to a group which was treated with estradiol alone.

A line of best fit was plotted for each compound which produced an estrogenic or anti-estrogenic response. Regression analysis was used to calculate each line. The slope of the response to each analog was compared to the slope of the estradiol response to determine parallelism in this assay system. The relative uterotropic activity of each compound was expressed as a percentage of estradiol activity.

Histological Preparation and Examination

Mouse uterine tissue was fixed in 10% formaldehyde, embedded in paraffin, sectioned on a microtome and stained with hematoxylineosin. Slides were examined with a compound light microscope and various measurements of uterine horn cross sections were made. These measurements, which were made on each cross section at several levels along the uterine horn, included:

(1) total uterine horn diameter or thickness, at two different points;

(2) endometrial thickness at two different points as measured from the endometrial-myometrial border to maximum invagination of the endometrium into the lumen of the uterine horn.

Photomicrographs of uterine horn cross sections and epithelial linings were taken with a camera attached to a compound light microscope.

Receptor Binding Assay

Uteri were removed from female Sprague-Dawley rats weighing approximately 250 g. The uteri were cleaned of connective tissue and homogenized in 5 vol. (w/v) ice-cold Tris buffer A containing 0.02M Tris (hydroxymethyl) aminomethane hydrochloride, 0.0015M disodium ethylenediamine tetraacetate, 0.25M sucrose and the pH was adjusted to 7.4. The tissue was homogenized using a motor driven ground glass tissue homogenizer placed in an ice-water bath. The homogenate was centrifuged at 100,00 X g for 1 hour at 4° C. using a swinging bucket rotor on an ultracentrifuge.

The supernatant (cytosol) was used immediately after preparation in the receptor binding assay. Incubations were conducted for 20 hours at 4° C. in a total volume of 0.5 ml of Tris buffer A containing 100°150 µl uterine cytosol, 0.025 µCi 2,4,6,7(n)-[$^3$H] 17B-estradiol (327 mCi/mg) and various concentrations of the test compounds. Each test compound was assayed at 3 concentrations over a range of $10^{-4}$ to $10^{-6}$ molar for the cyclopropyl analogs and $10^{-7}$ to $10^{-9}$ molar for the estradiol standard. The test compounds were dissolved in ethanol and in all cases the final concentration of the ethanol was less than 2% of the incubation media. At the end of the incubation period the cytosol-bound [$^3$H]-estradiol was separated from unbound [$^3$-H]-estradiol by the addition of 0.5 ml of a Dextran-coated charcoal solution (Tris buffer A containing 0.05% Dextran-70 and 0.5% Norit A charcoal). The assay tubes were vortexed and centrifuged at 500×g for 15 minutes. The [$^3$H]-estradiol concentration of a 0.5 ml aliquot of the supernatant was determined by liquid scintillation spectrometry. Counting times were automatically adjusted to obtain a counting error of less than 1% using a liquid scintillation counter. The [$^3$H]-estradiol displacement for each test compound was determined by linear regression analysis and plotted graphically. The relative receptor binding activity of each analog was determined using the ration: (concentration of unlabeled estradiol producing 70% displacement of [$^3$H]-estradiol/concentration of cyclopropyl analog producing 70% displacement of [$^3$H]-estradiol×100).

BIOLOGICAL RESULTS

The analogs set forth in Table I were tested to determine their estrogenic and anti-estrogenic activity using the uterotropic assay. The relative estrogenic activity of the analogs was determined to be that the estrogenic activity of analog VIII>analog IV>analog V. These analogs produced between 1.5% and 2.5% of the uterotropic response of estradiol on a molecular weight basis as reported in Table II hereinafter. Cyclopropyl analogs which displayed no estrogenic activity in the uterotropic assay were further tested for anti-estrogenic activity. As shown by the data of Table II, only analog II produced an antiestrogenic response.

TABLE II

ESTROGENIC, ANTI-ESTROGENIC AND RECEPTOR BINDING ACTIVITY OF THE CYCLOPROPYL ANALOGS

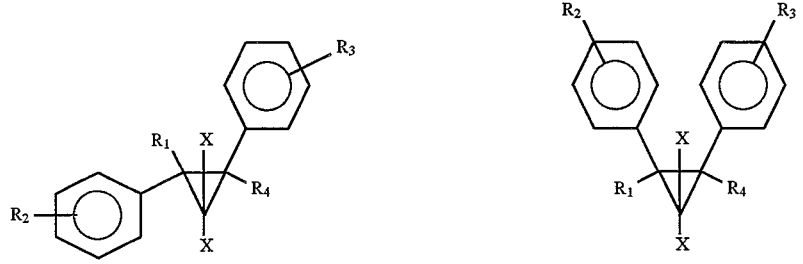

| Compound No. | Configuration | X | $R_1$ | $R_4$ | $R_2$ & $R_3$ | Relative Uterotropic Activity$_a$ | Anti-Estrogenic Activity$_b$ | Relative Receptor Binding Activity$_c$ |
|---|---|---|---|---|---|---|---|---|
| Estradiol | | | | | | 100 | — | 100 |
| Analog I | Trans | Cl | H | H | H | — | — | 0.02 |
| Analog II | Cis | Cl | H | H | H | — | 36 ug | 0.0086 |
| Analog III | Trans | H | $C_2H_5$ | $C_2H_5$ | $OCH_3$ | — | — | 0.4 |
| Analog IV | Trans | Cl | $C_2H_5$ | $C_2H_5$ | OH | 1.63 | — | 48.6 |
| Analog V | Trans | Cl | $C_2H_5$ | $C_2H_5$ | $OCOCH_3$ | 1.57 | — | 3.6 |

TABLE II-continued

ESTROGENIC, ANTI-ESTROGENIC AND RECEPTOR BINDING ACTIVITY OF THE CYCLOPROPYL ANALOGS

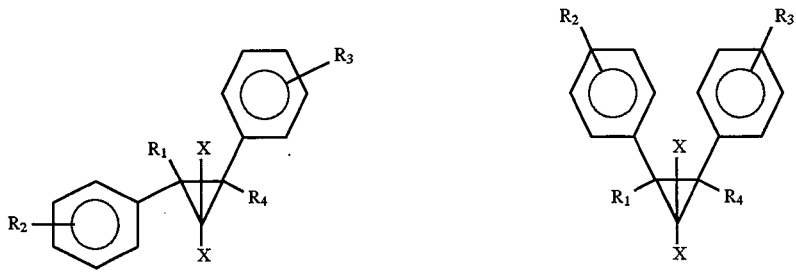

| Compound No. | Configuration | X | $R_1$ | $R_4$ | $R_2$ & $R_3$ | Relative Uterotropic Activity[a] | Anti-Estrogenic Activity[b] | Relative Receptor Binding Activity[c] |
|---|---|---|---|---|---|---|---|---|
| Analog VI   | Trans | Cl | H       | H       | $OCH_3$ | —    | — | 0.0038 |
| Analog VII  | Trans | Cl | $C_2H_5$ | $C_2H_5$ | $OCH_3$ | —    | — | 0.049  |
| Analog VIII | Trans | H  | $C_2H_5$ | $C_2H_5$ | OH      | 2.55 | — | 9.1    |
| Analog IX   | Cis   | H  | H       | H       | H       | —    | — | 0.0045 |
| Analox X    | Trans | H  | H       | H       | H       | —    | — | 0.0064 |

[a]Activity expressed as a percentage of estradiol activity.
[b]Dose of analog which would produce a 50% reduction in the uterotropic response to 0.04 ug estradiol.
[c]Concentration of estradiol that displaced 70% [$^3$H]-estradiol - concentration of analog that displaced 70% [$^3$H]-estradiol × 100.

Since the uterotropic response is a nonspecific measure of estrogenic activity, the uteri were examined histologically to confirm the estrogenic nature of the uterotropic response. Estradiol and the cyclopropyl analogs (IV and VIII) produced a significant (P<0.001) increase in uterine diameter and endometrial thickness which represent a specific estrogenic response (Table III).

TABLE III

HISTOLOGICAL EXAMINATION OF UTERINE SECTIONS

| Compound | Dose (ug) | Uterine Diameter (mm) Mean ± SD | Endometrial Thickness (mm) Mean ± SD |
|---|---|---|---|
| Control   | —    | 0.56 ± 0.15  | 0.16 ± 0.04  |
| Estradiol | 0.04 | 1.42 ± 0.24* | 0.49 ± 0.15* |
| Analog IV | 5.0  | 1.53 ± 0.19* | 0.48 ± 0.12* |
| Analog VIII | 5.0 | 1.30 ± 0.15* | 0.40 ± 0.07* |

*Significantly different from control P < 0.001.

The cyclopropyl analogs were tested for receptor binding activity and compared to the estradiol standard. All of the analogs were capable of displacing [$^3$H]-estradiol from the estrogen receptor. However, analogs IV, VIII, and V (in that order) displayed the greatest binding activity which ranged from 4% to 50% of the receptor binding activity produced by estradiol on a molecular weight basis (TabLe III).

The anti-tumor activity of the anti-estrogen (analog II) was examined using the 7,12-dimethylbenz(a) anthracene-induced mammary tumor assay in the rat in two separate experiments. In the first experiment the tumor data were expressed as both tumor volume/animal and tumor number/animal. Ovariectomy produced a slightly greater reduction in tumor volume during the first 3 weeks of the treatment period while tumor volume in the treated group remained essentially unchanged. Castration is known to cause regression of DMBA-induced tumors and was employed in the present study to verify the estrogen-dependent nature of the tumors in the population of rats included in this study. The number of tumors/animal increased in all 3 groups during the treatment period; however, both ovariectomy (OX) and analog II reduced tumor incidence to approximately the same extent when compared to the control group. The total weight gain during the treatment period in the control and treated groups was not significantly different; thus, suggesting that the anti-tumor activity of analog II was not the result of a general toxic effect of the compound. At the end of the treatment period all animals were sacrificed and the tumors were verified histologically to be adenocarcinomas.

The second tumor experiment was a parallel study which compared the anti-tumor activity of analog II to tamoxifen, which is a commercially available anti-estrogen which is presently used in the treatment of estrogen-dependent tumors in human subjects. The results of this parallel study are expressed in two ways: (A) percent of animals with decreased tumor volume; and (B) percent of animals with new tumors developing during the treatment period. Considering the influence of anti-estrogen treatment on decreased tumor volume analog II was found to significantly increase the percent of animals with a decreased tumor volume (P<0.02) between the 3rd and 5th week of therapy when compared to the control group. Similarly, tamoxifen significantly brought about a higher percentage of animals with a decreased tumor volume between the 5th and 7th week of therapy (P<0.02). There were no differences between the treatment groups and control groups in the percent of animals with no change in tumor volume. Thus, the overall impression is that analog II and tamoxifen are similar in their ability to reduce the growth of mammary tumors.

At the end of the treatment period 4 of the 8 analog II-treated animals had developed 9 new tumors while 6 of the 7 control rats developed 12 new tumors and 7 of the 8 tamoxifen-treated animals developed 17 new tumors. Thus, analog II protected 50% of the animals against new tumor development while only 12% of the tamoxifen-treated animals and 14% of the control animals were similarly protected. Thus, the above data indicates that analog II was more effective than tamoxifen in protecting animals against the development of new tumors during the treatment period.

Each of the cyclopropyl analogs set forth in this Example were found to bind, in a specific manner, to the estrogen receptor; and each of the analogs possessed little or no estrogenic activity relative to estradiol (e.g., less than about 1%, on a molar basis, of the estrogenic activity of estradiol). Thus, it is apparent that the anti-estrogenic cyclopropyl analogs as hereinbefore defined have potential as effective therapeutic agents in the treatment of estrogen-dependent tumors and as fertility agents. Further, the biological results relating to the anti-estrogenic properties of analog II (the cis-isomer) were totally unexpected since the trans-isomer of stilbene and stilbenediol derivatives (which contains a double bond) have heretofore been known to possess greater activity than the corresponding cis-isomer. Further the most active established anti-estrogens (i.e., the di- and triarylethylenes are known to be the trans-isomers.

EXAMPLE 4

A series of cyclopropyl analogs were prepared using the procedures A, B, and C set forth in Example I, and the cyclopropyl analogs so prepared were subjected to a series of experiments to determine the estrogen receptor binding activity of each of the analogs tabulated in Table IV. The estrogen receptor binding activities of the analogs of Table IV are reported in Table V.

BIOLOGICAL RESULTS

Each analog as set forth in Table IV was tested initially in the uterotropic assays for estrogenic and anti-estrogenic activity as described in Example I. It was determined that none of the analogs listed in Table IV displayed estrogenic or anti-estrogenic activity in the assay system employed.

The cyclopropyl analogs listed in Table IV, were further tested for receptor binding activity as described in Example I. The data tabulated in Table V indicates that all of the analogs listed in Table IV were capable of specific binding to the estrogen receptor.

TABLE IV

CYCLOPROPYL ANALOGS

| Analog No. | Chemical Name |
|---|---|
| XI | 1,1-dichloro-trans-2-methyl-2,3-(4,4'-dimethoxydiphenyl)cyclopropane |
| XII | 1,1-dichloro-trans-2,3-dimethyl-2,3-(4,4'-dimethoxydiphenyl)cyclopropane |
| XIII | 1,1-dichloro-trans-2-methyl-2,3,-diphenyl-cyclopropane |
| XIV | 1,1-dichloro-trans-2,3-dimethyl-2,3-diphenylcyclopropane |
| XV | 1,1-dichloro-cis-2-methyl-2,3-diphenyl-cyclopropane |
| XVI | 1,1-dichloro-cis-2,3-dimethyl-2,3-diphenylcyclopropane |
| XVII | 1-methyl-trans-1,2-(4,4'-dimethoxy-diphenyl)cyclopropane |
| XVIII | trans-1,2-dimethyl-1,2-(4,4'-dimethoxy-diphenyl)cyclopropane |
| XIX | trans-1-methyl-1,2-diphenylcyclopropane |
| XX | trans-1,2-Dimethyl-1,2-diphenylcyclopropane |
| XXI | cis-1-methyl-1,2-diphenylcyclopropane |

TABLE V

RECEPTOR BINDING ACTIVITY OF THE CYCLOPROPYL ANALOGS

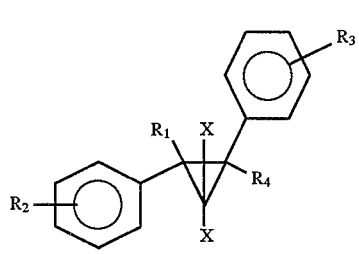 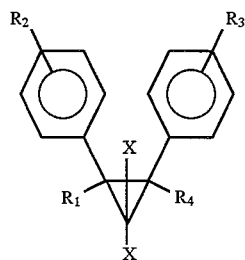

| Compound No. | Isomer Configuration | X | $R_1$ | $R_4$ | $R_2$ & $R_3$ | Relative Binding Activity[a] (% Estradiol Response) |
|---|---|---|---|---|---|---|
| Estradiol | | | | | | 100 |
| XI | trans | Cl | $CH_3$ | H | $O-CH_3$ | $8.3 \times 10^{-5}$ |
| XII | trans | Cl | $CH_3$ | $CH_3$ | $O-CH_3$ | $5.9 \times 10^{-4}$ |

TABLE V-continued

RECEPTOR BINDING ACTIVITY OF THE CYCLOPROPYL ANALOGS

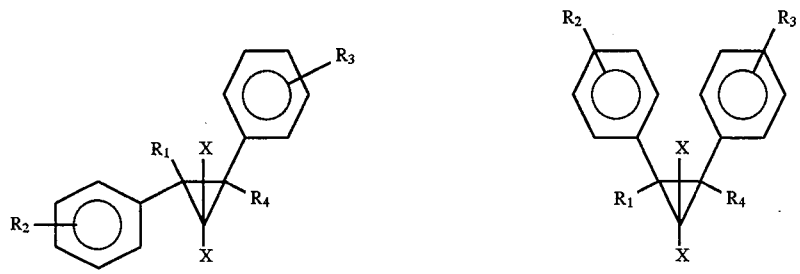

| Compound No. | Isomer Configuration | X | $R_1$ | $R_4$ | $R_2$ & $R_3$ | Relative Binding Activity[a] (% Estradiol Response) |
|---|---|---|---|---|---|---|
| XIII | trans | Cl | $CH_3$ | H | H | $5.3 \times 10^{-4}$ |
| XIV | trans | Cl | $CH_3$ | $CH_3$ | H | $5.1 \times 10^{-4}$ |
| XV | cis | Cl | $CH_3$ | H | H | $6.3 \times 10^{-4}$ |
| XVI | cis | Cl | $CH_3$ | $CH_3$ | H | $5.5 \times 10^{-4}$ |
| XVII | trans | H | $CH_3$ | H | $O-CH_3$ | $7.3 \times 10^{-4}$ |
| XVIII | trans | H | $CH_3$ | $CH_3$ | $O-CH_3$ | $2.2 \times 10^{-3}$ |
| XIX | trans | H | $CH_3$ | H | H | $1.5 \times 10^{-4}$ |
| XX | trans | H | $CH_3$ | $CH_3$ | H | $1.1 \times 10^{-4}$ |
| XXI | cis | H | $CH_3$ | H | H | $8.0 \times 10^{-4}$ |

[a] $\dfrac{\text{Concentration of estradiol that displaced 50\% [3}_H\text{]-estradiol}}{\text{Concentration of analog that displaced 50\% [3}_H\text{]-estradiol}} \times 100$ Each of the anti-estrogenic cyclopropyl analogs set forth in this example was found to bind, in a specific manner, to the estrogen receptor, and each of the analogs possessed no estrogenic activity. Thus, it is apparent that the anti-estrogenic cyclopropyl analogs as hereinbefore defined have potential as effective therapeutic agents in the treatment of estrogen dependent tumors and as fertility agents. However, analogs IV, V, and VIII exhibited substantially greater estrogen-receptor binding activity and uterotropic activity than the other analogs of Tables I and II (i.e., analogs IV, V and VIII had greater than about 1%, on a molar basis of the estrogenic activity of estradiol) and thus would not be suitable as fertility agents. Thus, analogs IV, V and VIII are specifically excluded from the compounds represented by Structure I, which would be suitable as fertility agents in the treatment of infertile female subjects.

EXAMPLE 5

The compounds 1-1-dichloro-cis-2,3-diphenylcyclopropane (analog II) and 1-1-dibromo-trans-2,3-diphenylcyclopropane (analog XXII) were tested to determine their estrogenic and anti-estrogenic activity using the uterotropic assay.

The assay for estrogenic activity employed immature Sprague-Dawley rats approximately 21 days old, weighing 40–50 g. The animals were randomly distributed into groups containing three rats each. The test compounds were dissolved separately in corn oil and administered subcutaneously in a volume of 0.1 ml. Control animals were treated with the same volume of corn oil alone.

All animals were treated daily for three consecutive days. Animals receiving the test compounds received a total dose of 100 ug of test compound. On the fourth day, the animals were sacrificed and the uteri carefully dissected, blotted lightly and weighed to the nearest 0.1 mg. Body weights were also recorded. The relative estrogenic activity of the test compounds was expressed in terms of the percentage change in uterine weight in treated animals as compared to Uterine weight in control animals.

The uterotropic assay was also used to evaluate the anti-estrogenic activity of the test compounds. The anti-estrogenic assay was conducted as described above for estrogenic activity, except that each animal treated with test compounds also received a standard stimulating dose of estradiol, 0.2 µg total dose over three days. The test compounds and estradiol were administered separately at different injection sites in order to minimize possible physical interaction or reduced absorption of other compounds. Control animals received only the standard stimulating dose of estradiol. The anti-estrogenic activity of the test compounds was expressed as a percentage change in estrogen-stimulated uterine weight as compared to the uterine weight of an estrogen-stimulated control animal.

The results of these tests are shown in Table VI. The results reveal that analog XXII displays anti-estrogenic activity, although not to the extent of that displayed by analog II. Further, the results reveal both analog II and analog XXII do not display estrogenic activity, in contrast to many other anti-estrogens now in clinical use. Thus, it is believed that analog XXII is suitable for use as an anti-tumor, fertility and anti-estrogen agent in accordance with the present invention.

TABLE VI

ESTROGENIC AND ANTI-ESTROGENIC ACTIVITY OF CYCLOPROPYL ANALOGS

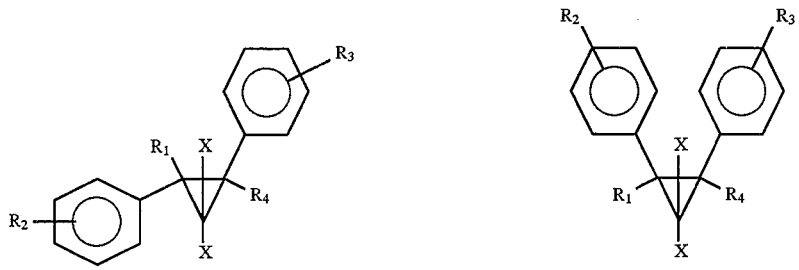

| Compound No. | Configuration | X | R₁ | R₄ | R₂ & R₃ | Estrogenic Assay % change in control uterine weight | Antiestrogenic Assay % change in estrogen stimulated uterine weight |
|---|---|---|---|---|---|---|---|
| Analog II | cis | Cl | H | H | H | −29.5% | −38.5% |
| Analog XXII | trans | Br | H | H | H | −0.4% | −25.1% |

PREPARATION OF DIPHENYLCYCLOPROPANES HAVING SUBSTITUTED ALKOXY SIDE CHAINS

Example 6

Preparation of (Z)-1,1-Dichloro-2-[4-(2-methanesulfonyloxyethoxy) phenyl]-3-phenylcyclopropane (Compound 7)

A mixture of p-hydroxybenzaldehyde (40.30 g, 0.33 mol), 2-chloroethyl methyl ether (31.20 g 0.33 mol) and $K_2CO_3$ (45.61 g, 0.33 mol) in DMF (100 mL) was refluxed for 12 hours. The resulting orange mixture was diluted with water (100 mL) and extracted three times with 50 mL of $CHCl_3$. The organic layers were combined and washed with 5% NaOH, brine and dried over anhydrous $MgSO_4$. It was filtered and evaporated in vacuo to give brown liquid which was distilled on the Kugelrohr distillation apparatus to obtain yellowish liquid (51.40 g, 87%) at room temperature but solid in the cold. NMR ($CDCl_3$) δ 3.40 (s, 3H $OCH_3$), 3.60–3.90 (m, 2H, $OCH_2$), 4.00–4.20 (m, 2H, $OCH_2$), 6.70 and 7.05 (dd, 4H, substituted ArH), 7.20–7.50 (m, 5H, ArH), 7.95 (s, 1H, C=CH) . This procedure produces (Z)-α-Phenyl-β-[4- (2-methoxy)ethoxy] cinnamic acid.

A 500 mL, three necked, round bottom flask equipped with a condenser, with a gas trap, a thermometer and a magnetic stirrer was utilized. To a solution of (Z)-α-Phenyl-β-[4- (2-methoxy) ethoxy] cinnamic acid (20.00 g, 0.07 mol) in quinoline (90.41 g, 0.70 mol) was added copper chromite (1.46 g, 0.005 mol) and heated. Carbon dioxide evolved when the temperature reached 190° C. The mixture was kept within 200°–210° C. for 3 hours, cooled to room temperature and filtered under vacuum. The black mixture was transferred to a separatory funnel with 100 mL of $Et_2O$ and extracted with five 50 mL portions of 20% HCl solution to remove the residual quinoline. The $Et_2O$ layers were washed with brine, dried over $MgSO_4$ and concentrated in vacuo. The resulting brown oil was purified by flash chromatography (silica gel, 50/50 $CH_2Cl_2$/petroleum ether) to obtain cis stilbene 4 (15.61 g, 91%) as a very light yellow oil. NMR ($CDCl_3$) δ 3.40 (s, 3H, $OCH_3$), 3.60–3.90 (m, 2H, $OCH_2$), 4.00–4.20 (m, 2H, $OCH_2$), 6.55 (s, 2H, C=CH), 6.80 and 7.20 (dd, 4H, substituted ArH), 7.30 (s, 5H, ArH). This procedure produces (Z)-1-[4-(2-methoxyethoxy)phenyl]-2-phenylethylene.

To (Z)-1-[4-(2-methoxyethoxy)phenyl]-2-phenylethylene (15.61 g, 0.06 mol) dissolved in $CHCl_3$ (193 mL) was added triethylbenzyl-ammonium chloride (0.98 g, 0.004 mol), chilled 40% NaOH solution (96.00 g, 2.40 mol) was added slowly through a dropping funnel according to the method of Dehmlow and Schonefeld, *J. Lebigs Ann Chem.*, 744:42 (1971) and the mixture stirred for 80 hours. The resulting brown emulsion was poured onto 200 mL water in a separatory funnel and the layers were separated, the aqueous layer was extracted with three 50 mL portions of $CH_2Cl_2$, the combined organic extracts were washed with brine, dried over $MgSO_4$, filtered and evaporated in vacuo to obtain a dark brown oil which was purified by flash chromatography (50:50 $CH_2Cl_2$/petroleum ether) to give a colorless oil (19.70 g, 80%). NMR ($CDCl_3$) δ 3.30 (s, 2H. ArCH), 3.50 (s, 3H, $OCH_3$), 3.65–3.85 (m, 2H, $OCH_2$), 4.00–4.25 (m, 2H, $OCH_2$), 6.85–7.40 (m, 9H, ArH). This procedure produces (Z)-1,1-Dichloro-2-[4-(-methoxyethoxy)phenyl]-3-phenylcyclopropane.

To (Z)-1,1-Dichloro-2-[4-(2-methoxyethoxy)phenyl]-3-phenylcyclopropane (14.10 g, 0.04 mol) in $CH_3CN$ (100 mL) was added sodium iodide (25.07 g, 0.17 g). The reaction flask was fitted with a gas trap, an argon inlet and a rubber septum. The reaction flask was then flushed with argon. By means of a syringe, chlorotrimethylsilane (21 mL) was injected into the reaction flask through the rubber septum and the mixture stirred at room temperature for 24 hours. Water (100 mL) was then added to the mixture and extracted with three 50 mL portions of ethyl acetate. The organic extracts were combined and washed with sodium thiosulfate solution till the organic extract became colorless, then dried over anhydrous $MgSO_4$ and evaporated in vacuo to obtain an oil. The oil was purified by flash chromatography and eluted with $CH_2Cl_2$ to give a colorless oil (10.79 g, 80%). NMR ($CDCl_3$) δ 2.20. (broad, 1H, OH), 3.30 (s, 2H, ArCH), 3.90–4.20 (m, 4H, $OCH_2CH_2OH$), 6.80–7.50 (m, 9H, ArH). This procedure produces (Z)-1,1-Dichloro-2-[4-(2-hydroxyethoxy)-phenyl]-3-phenylcyclopropane.

Triethylamine (14.87 g, 0.15 mol) was added to a solution (Z)-1,1-Dichloro-2-[4-(2-hydroxyethoxy)-phenyl]-3-phenylcyclopropane (10.78 g, 0.03 mol) and methanesulfonyl chloride (16.81 g, 0.15 mol) in THF (50 mL) at 0° C. After 1 h water (50 mL) was added to the reaction mixture and transferred to a separatory funnel. The mixture was extracted three times with 30 mL portions of ethyl acetate, dried over $MgSO_4$ and concentrated in vacuo to give a light yellow oil. The oil was purified by flash chromatography (50:50 $CH_2Cl_2$/petroleum ether) to give a colorless oil (11.65 g, 87%). NMR ($CDCl_3$) δ 3.10 (s, 3H, $OSO_2CH_3$), 3.30 (s, 2H, ArCH), 4.10–4.30 (m, 2H, $OCH_2OSO_2CH_3$), 4.50–4.70 (m, 2H, $ArOCH_2$), 6.80–7.40 (m, 9H, ArH).

EXAMPLE 7

Preparation of (Z)-1,1-Dichloro-2-[4-[2-(dimethylamino) ethoxy]-phenyl]-3-phenylcyclopropane (Compound 8)

To the (Z)-1,1-Dichloro-2-[4-(2-methanesulfonyloxyethoxy) phenyl]-3-phenylcyclopropane (1.00 g, 0.003 mol) in 25 mL $CH_3CN$ was added dimethylamine hydrochloride (2.45 g, 0.03 mol) and the mixture cooled in dry ice/acetone bath for 25 min. Flame dried $K_2CO_3$ (8.29 g, 0.06 mol) was then added and the flask stoppered with a rubber septum so as to trap the gaseous dimethylamine. The slurry mixture was stirred at room temperature for 48 h after which 25 mL of water was added and extracted with three portions of 10 mL $Et_2O$. The $Et_2O$ extracts were combined, dried over $MgSO_4$ and evaporated in vacuo, the residue was purified by flash chromatography and eluted with EtOAc to give a light yellowish oil. The oil was dissolved in 25 mL $Et_2O$ and extracted with 10 mL portions of 30% HCl solution until the $Et_2O$ layer became clear. The combined aqueous extracts were treated with 20% NaOH solution to pH 11, and extracted with three portions of 20 mL $Et_2O$. The combined $Et_2O$ extracts were washed with water, dried over $MgSO_4$ and concentrated in vacuo to obtain a light yellow oil (0.60 g, 71%). NMR ($CDCl_3$) δ 2.35 (s, 6H, $N(CH_3)_2$), 2.70 (t, 2H, $CH_2N$), 3.30 (s, 2H, ArCH), 4.05 (t, 2H, $OCH_2$), 6.90–7.40 (m, 9H, ArH).

Citrate Salt: The oil (Z)-1,1-Dichloro-2-[4-[2-(dimethylamino) ethoxy]-phenyl]-3-phenylcyclopropane was dissolved in hot EtOH and treated with an equal molar amount of citric acid in hot EtOH. The citrate salt was recrystallized from EtOH and obtained as a white powder in 81% yield, mp: 67°–68° C.

EXAMPLE 8

Preparation of (Z)-1,1-Dichloro-2-[4-[2-(diethylamino) ethoxy]-phenyl]-3-phenylcyclopropane (Compound 9)

Diethylamine (10 mL) and $Et_3N$ (10 mL) were added to a solution of (Z)-1,1-Dichloro-2-[4-(2-methanesulfonyloxyethoxy)phenyl]-3-phenylcyclopropane (1.00 g, 0.003 mol) in acetonitrile (20 mL). The orange solution was stirred at room temperature for 48 h after which the volatile components were evaporated in vacuo and the residue purified by flash chromatography eluting with EtOAc to give an orange oil. Further purification was carried out by acid/base extraction as in the procedure for (Z)-1,1-Dichloro-2-[4-[2-(dimethylamino) ethoxy]-phenyl]-3-phenylcyclopropane to obtain a light orange oil (0.66 g, 70%) NMR ($CDCl_3$) δ 1.15 (t, 6H, $NCH_2CH_3$), 2.50–3.00 (m, 6H, $OCH_2CH_2$ and $NCH_2CH_3$), 3.30 (s, 2H, ArCH), 4.10 (t, 2H, $OCH_2$), 6.90–7.40 (m, 9H, ArH).

Citrate Salt: The oil (Z)-1,1-Dichloro-2-[4-[2-(diethylamino)-ethoxy]-phenyl]-3-phenylcyclopropane was dissolved in hot EtOH and treated with an equal amount of citric acid in hot EtOH. The citrate salt was recrystallized from EtOH and obtained as a white powder in 83% yield, mp: 101°–102° C.

EXAMPLE 9

Preparation of (Z)-1, 1-Dichloro-2-[4-[2-(piperidino) ethoxy]-phenyl]-3-phenylcyclopropane (Compound 10)

This compound was prepared according to the procedure used to synthesize (Z)-1,1-Dichloro-2-[4-[2-(diethylamino) ethoxy]-phenyl]-3-phenylcyclopropane described herein using (Z)-1,1-Dichloro-2-[4-(2-methanesulfonyloxyethoxy) phenyl]-3-phenylcyclopropane (1.00 g, 0.003 mol) and piperidine (10 mL). The compound was obtained as a light orange oil (0.84 g, 87%). NMR ($CDCl_3$) δ 1.40–1.70 (m, 6H, ring $CH_2$ nonadjacent to N), 2.40–2.60 (broad m, 4H, $CH_2$ adjacent to N), 2.75 (t, 2H, $CH_2N$), 3.30 (s, 2H, ArH), 4.10 (t, 2H,$OCH_2$), 6.80–7.40 (broad m, 9H, ArH).

Citrate Salt: The oil (Z)-1,1-(Dichloro-2-[4-[2-(piperidino)-ethoxy]-phenyl]-3-phenylcyclopropane was dissolved in hot EtOH and treated with an equal amount of citric acid in hot EtOH. The citrate salt was recrystallized from EtOH and obtained as a white powder in 85% yield, top: 96°–100° C.

EXAMPLE 10

Preparation of (Z)-1,1-Dichloro-2-[4-[2-(N-methylpiperazino) ethoxy]-phenyl]-3 phenylcyclopropane (Compound 11)

This compound was prepared according to the procedure used to synthesize (Z)-1,1-Dichloro-2-[4-(2-diethylamino) ethoxy]-phenyl]-3-phenylcyclopropane described herein using (Z)-1,1-Dichloro-2-[4(2-methanesulfonyloxyethoxy) phenyl-3-phenylcyclopropane (1.00, g 0.003 mol) and N-methyl piperazine (10 mL). The product was obtained as a colorless oil (0.82 g, 81%). NMR ($CDCl_3$) δ 2.27 (s, 3H, $NCH_3$), 2.39–2.70 (broad m, 8H, ring $CH_2$), 2.80 (t, 2H, $CH_2N$), 3.30 (s, 2H, ArCH), 4.05 (t, 2H, $OCH_2$), 6.90–7.40 (m, 9H, ArH).

Citrate Salt: The oil (Z)-1,1-Dichloro-2-[4-[2-(N methylpiperazino) ethoxy]-phenyl]-3-phenylcyclopropane was dissolved in hot EtOH and treated with an equal amount of citric acid in hot EtOH. The citrate salt was recrystallized from EtOH and obtained as a white powder in 90% yield, mp: 101°–102° C.

PREPARATION OF MONOMETHYL AND DIMETHYL DIPHENYLCYCLOPROPANES HAVING SUBSTITUTED ALKOXY SIDE CHAINS

EXAMPLE 11

Preparation of 2-Methyl Compounds

I. Preparation of Starting Monomethyl Olefin (Z/E-1-{4-[2,3,5,6-tetrafluoro-4-(trifluoromethyl) phenoxy]phenyl}-1-methyl-2-phenyl ethene)

Figure 1B:
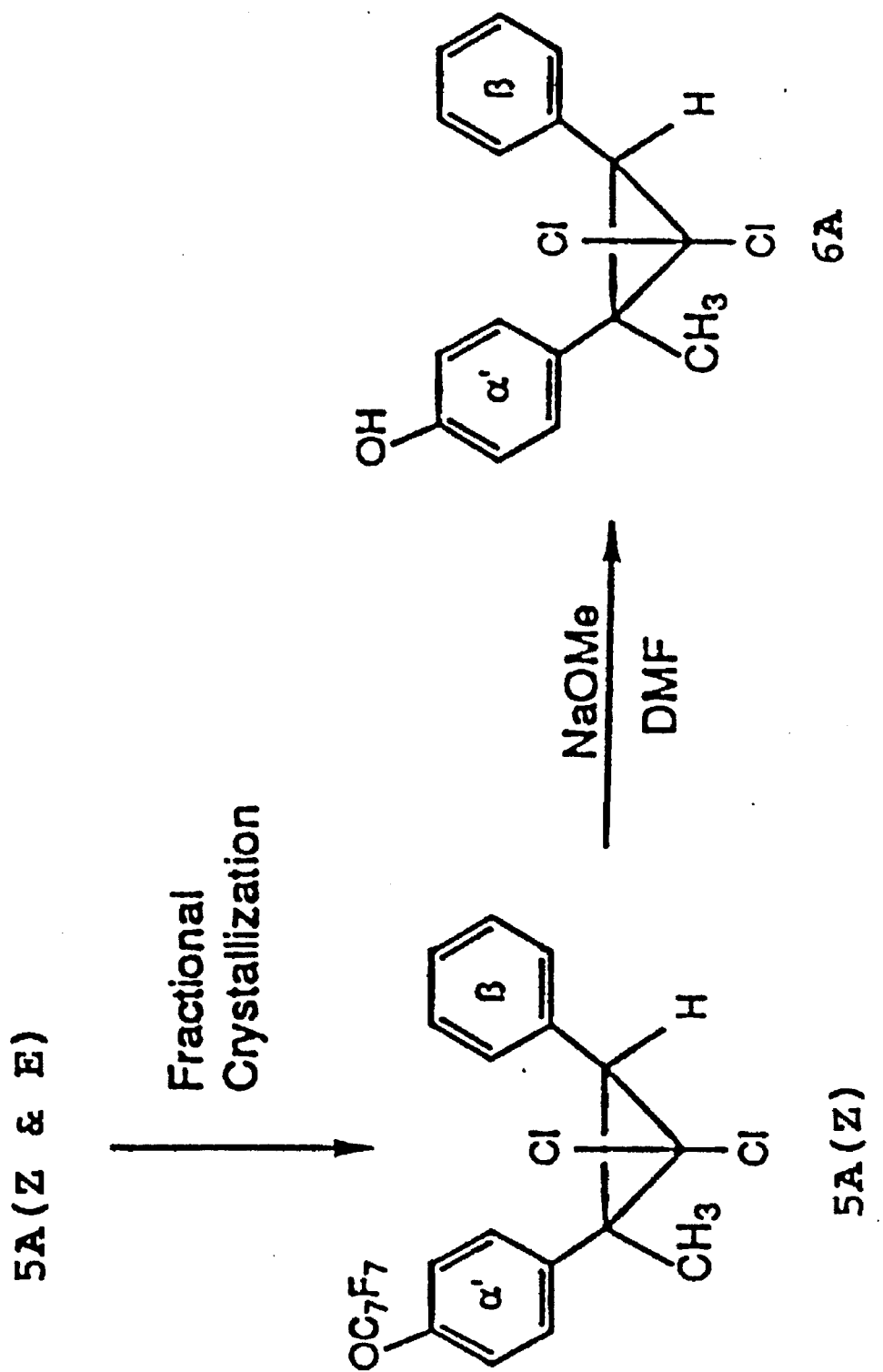
FIG. 1B is an intermediate portion of Scheme I.
Figure 1C:
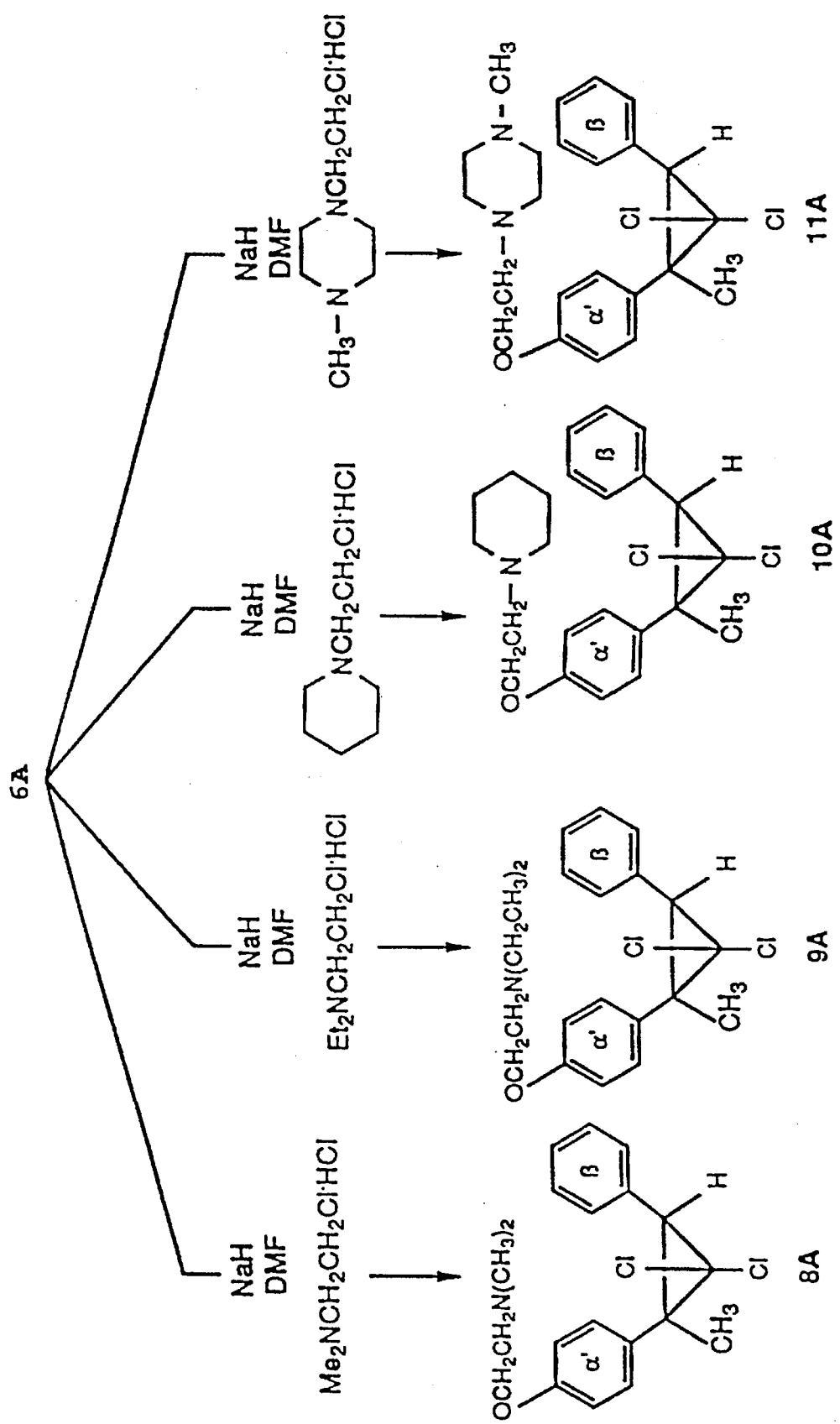
FIG. 1C is the final portion of Scheme I.

Preparation of four 2-methyl diphenylcyclopropanes (Compounds 8A-11A) is schematicany shown in FIGS. 1A, 1B and 1C. To a flame-dried, three necked 500 ml round bottom flask equipped with a stir bar, reflux condenser, and pressure-equilibrating dropping funnel is added magnesium filings and 4-(perfluorotolyloxy) phenyl bromide (1:1.5) to freshly distilled THF (from Calcium Hydride). Dibromoethane dissolved in THF is then added slowly via the dropping funnel over several hours following the complete addition of dibromoethane and the disappearance of magnesium, benzyl methyl ketone dissolved in THF is injected into the reaction mixture. There the reaction is stirred at room temperature for at least 60 hours. Subsequently, the mixture is transferred to a separatory funnel and 0.5M HCl is added. The organic phase is removed and the aqueous phase extracted three times with 25 ml portions of diethyl ether. Combined organic layers are dried over anhydrous magnesium sulfate, filtered, and the solvent removed to yield an oil. The oil is dissolved in benzene and p-toluenesulfonic acid is added. The mixture is reflexed for 18 hours. Upon cooling to room temperature, water is added to the reaction vessel and the solution is transferred to a separatory funnel. The organic phase is removed and is extracted with 3 portions of benzene. The combined benzene layers are dried over anhydrous magnesium sulfate, filtered, and the solvent is removed to yield an oil. The oil is purified by column chromatography .(silica gel 1:1 petroleum ether/methylene chloride). The oil contains the mixture of the Z and E-diastereomers of the ethene (Z/E-1-{4-[2,3,5,6-tetrafluoro-4-(trifluoromethyl) phenoxy]phenyl}-1-methyl-2-phenyl ethene).

II. Preparation of the Monomethyl Cyclopropane Intermediate (Z/E-1,1-dichloro-2-{4-[2,3,5,6-tetrafluoro-4-(trifluoromethyl) phenoxy]phenyl}-2-methyl-3-phenylcyclopropane)

A molar ratio (1:10) of triethylbenzylammonium chloride to the starting olefin from step I above (Z/E-1-{4-[2,3,5,6-tetrafluoro-4-(trifluoromethyl) phenoxy]phenyl}-1-methyl-2-phenyl ethene) is dissolved in excess chloroform (10 times the molar concentration of olefin) contained in a three neck flask fitted with an air condenser and dropping funnel. The flask is cooled in an ice water bath and a 33–50% aqueous sodium hydroxide solution (sodium hydroxide-chloroform, 2:1) is added dropwise while the mixture is magnetically stirred. After the addition is completed, the ice bath is removed and stirring continued for 120 hrs. The dark mixture is diluted with excess water and the aqueous layer is separated and extracted three times with chloroform. The chloroform extracts are combined, washed three times with water, dried over anhydrous magnesium sulfate, and filtered to remove the drying agent. The chloroform is removed under reduced pressure, yielding a dark liquid or solid which is purified by chromatography and recrystallization. The Z & E isomers are then separated by fractional crystallization. The diastereomers are readily identified by proton NMR spectroscopy.

III. Preparation of 2-Methyl Derivatives with Side Chains

To a solution of the Z isomer of the heptafluoro-tolyloxycyclopropane formed above (Z-1,1-dichloro-2-{4-[2,3,5,6-tetrafluoro-4-(trifluoromethyl)phenoxy]phenyl}-2-methyl-3-phenylcyclopropane) in dry N,N-dimethyl formamide is added sodium methoxide and the mixture is stirred at 40° C. for 2 hours. The mixture is then partitioned between diethyl ether and diluted sulfuric acid (0.05M). The ether layer is dried over anhydrous magnesium sulfate and concentrated. The crude phenol (compound without the heptafluorotolyl group) is dissolved in dry N,N-dimethylformamide under nitrogen, sodium hydride is added and the mixture is stirred and heated at 40° C. Then a side chain reagent (one of N,N-dimethylaminoethylchloride HCl salt; N,N-diethylaminoethylchloride HCl salt; 2-piperidinoethylchloride HCl salt; or 2-(N-methylpiperazino)ethylchloride HCl salt) is added in small portions over 30 minutes, and the mixture is maintained at 40° C. for an additional 30 minutes. Excess sodium hydride is destroyed by the addition of water and the resulting solution partitioned between ether and water. The aqueous layer is further extracted with ether, the combined ether solutions are dried over anhydrous magnesium sulfate and the solvent is evaporated. Chromatography of the residues give the respective desired side chain derivative of the 2-methyl cyclopropane compounds. Although it is preferred to use the Z isomer form of the intermediate, it will be readily apparent to one of ordinary skill in the art that the E isomer intermediate can also be used in the process thereby forming E isomer versions of the resulting products.

When N,N-dimethylaminoethylchloride MCl salt is used in Step III above as the side chain reagent a modified 2-methyl version of Compound 8, designated herein as Compound 8A and shown below, is formed:

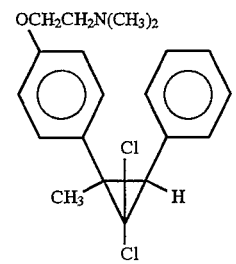

(Z)-1,1-Dichloro-2-{4-[2-(dimethylamino)ethoxy]-phenyl}-2-methyl-3-phenycyclopropane (Compound 8A)

When N,N-diethylaminoethylchloride HCl salt is used in Step III above as the side chain reagent a modified 2-methyl version of Compound 9, designated herein as Compound 9A and shown below, is formed:

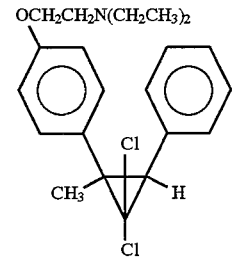

(Z)-1,1-Dichloro-2-{4-[2-(diethylamino)ethoxy]-phenyl}-2-methyl-3-phenylcyclopropane (Compound 9A)

When 2-piperidinoethylchloride HCl salt is used in Step III above as the side chain reagent a modified 2-methyl version of Compound 10, designated herein as Compound 10A and shown below, is formed:

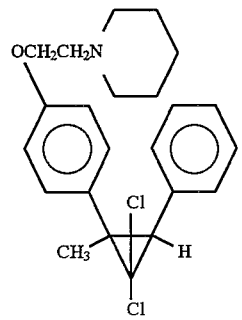

(Z)-1,1-Dichloro-2-{4-[2-(piperidino)ethoxy]-phenyl}-2-methyl-3-phenylcyclopropane (Compound 10A)

When 2-(N-methylpiperazino) ethylchloride HCl salt is used in Step III above as the side chain reagent a modified 2-methyl version of Compound 11, designated herein as Compound 11A and shown below, is formed:

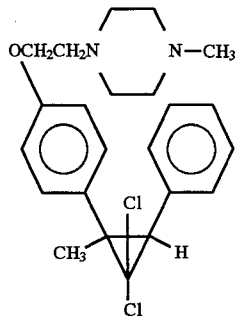

(Z)-1,1-Dichloro-2-{4-[2-(N-methylpiperazino) ethoxy]-phenyl}-2-methyl-3-phenylcyclopropane (Compound 11A)

EXAMPLE 12

Preparation of 3-Methyl Compounds

I. Preparation of Starting Monomethyl Olefin (Z/E-1-{4-[2,3,5,6-tetrafluoro-4-(trifluoromethyl) phenoxy]phenyl}-2-methyl-2-phenyl ethene)

Figure 2A:
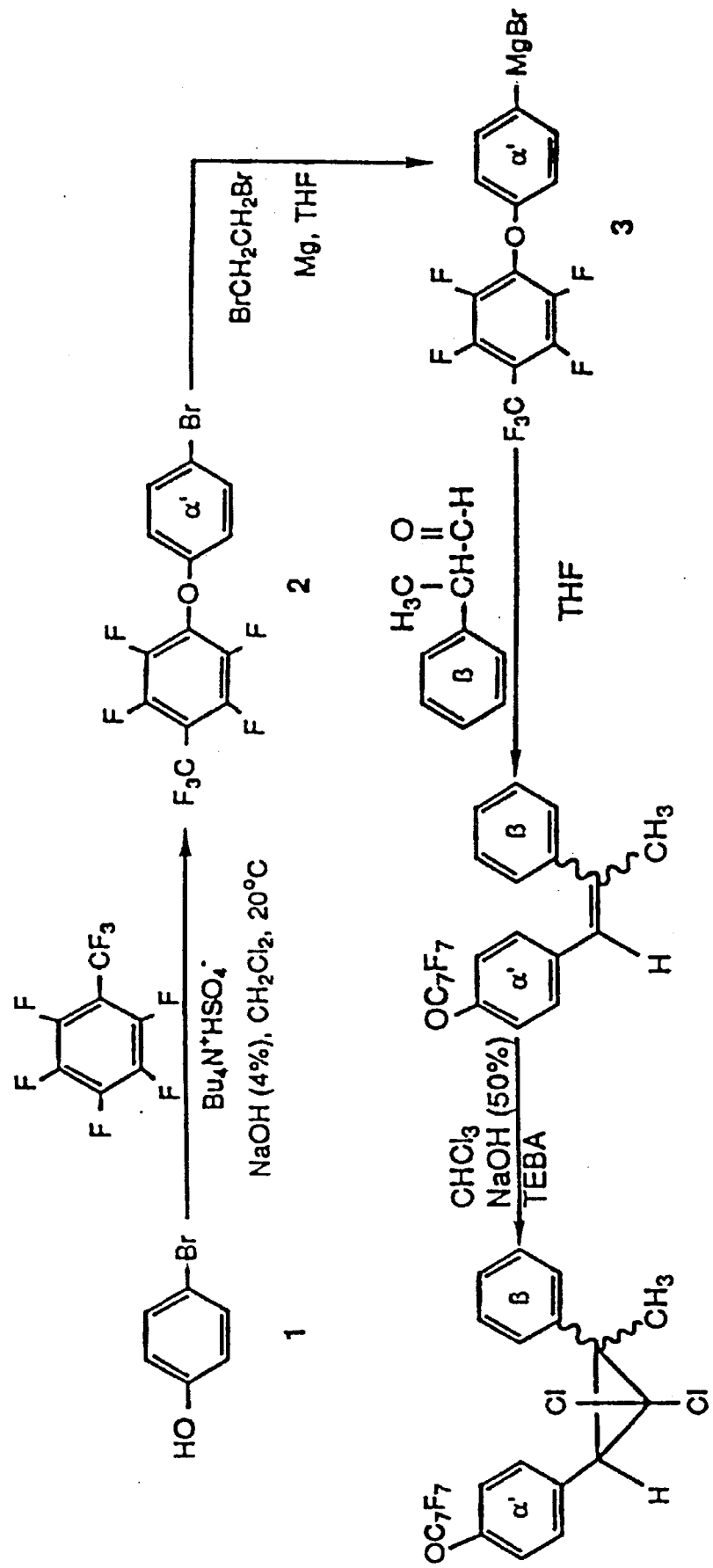
FIG. 2A is a portion of a scheme (Scheme II) shwoing a process for synthesizing four 3-methyl diphenylcyclopropanes, each having a different side chain.
Figure 2B:
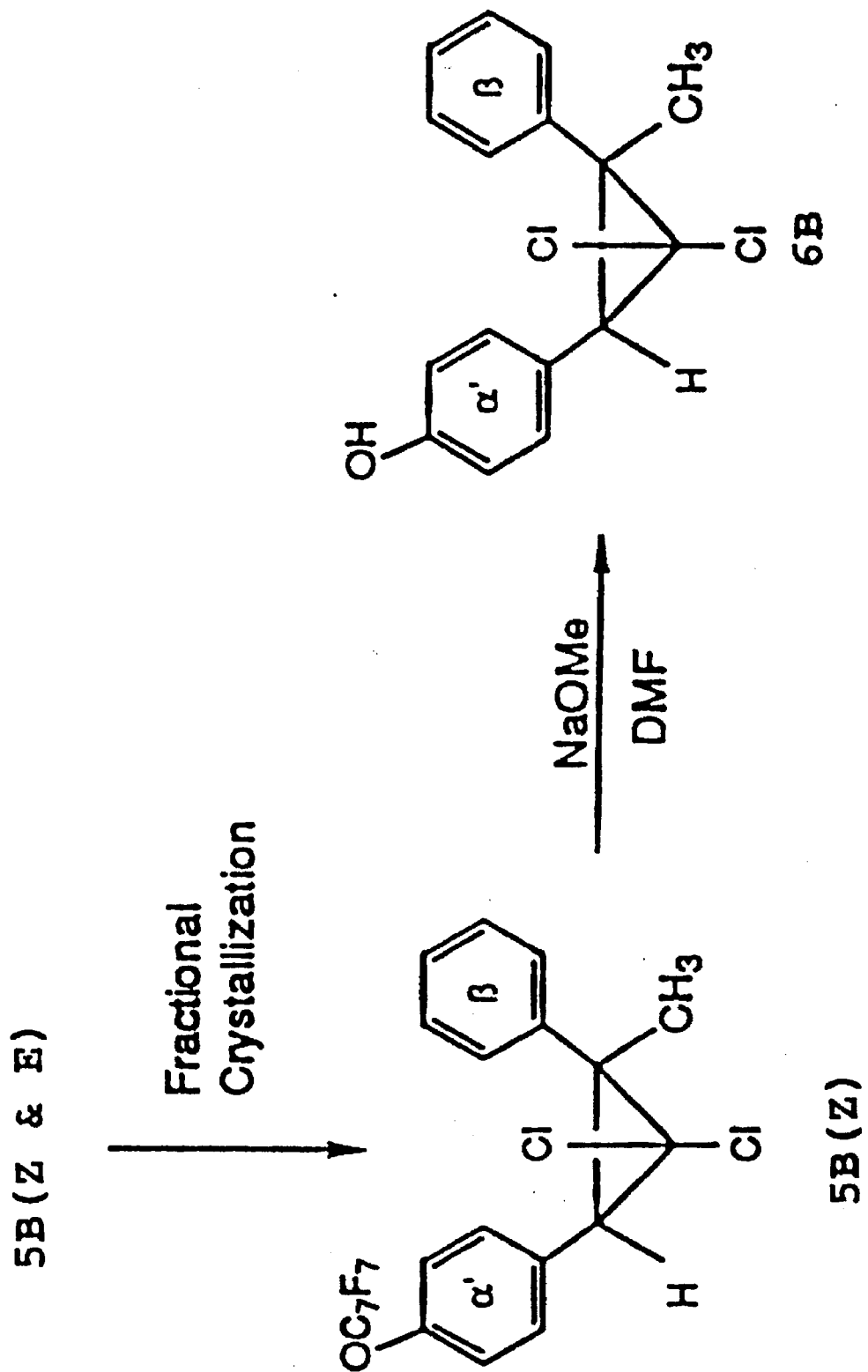
FIG. 2B is an intermediate portion of Scheme II.
Figure 2C:
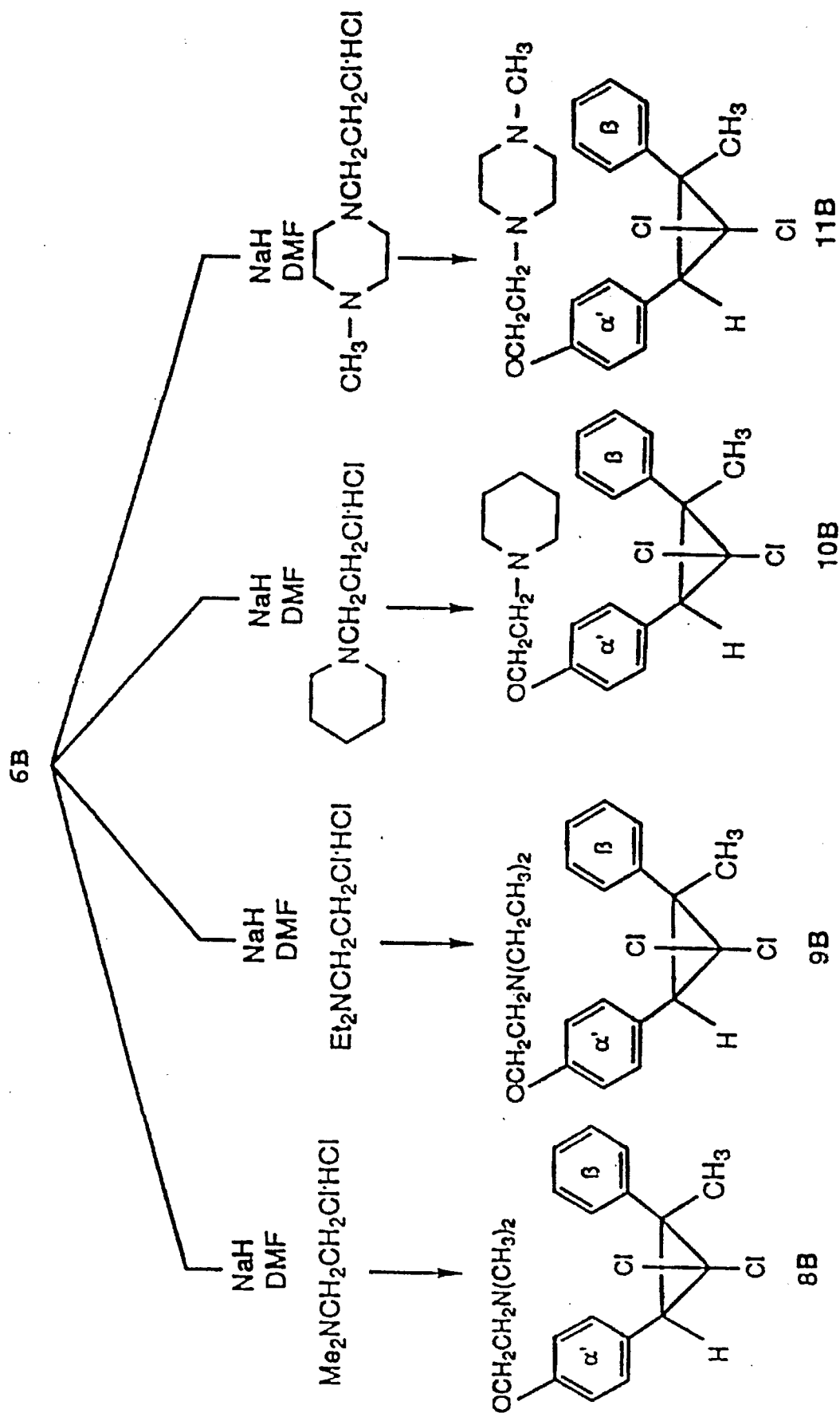
FIG. 2C is the final portion of Scheme II.

Preparation of four 3-methyl diphenylcyclopropanes (Compounds 8B-11B) is schematically shown in FIGS. 2A, 2B and 2C. To a flame-dried, three necked 500 ml round bottom flask equipped with a stir bar, reflux condenser, and pressure-equilibrating dropping funnel is added magnesium filings and 4-(perfluorotolyloxy) phenyl bromide (1:1.5) to freshly distilled THF (from Calcium Hydride). Dibromoethane dissolved in THF is then added slowly via the dropping funnel over several hours following the complete addition of dibromoethane and the disappearance of magnesium, α-phenyl propionaldehyde dissolved in TEF is injected into the reaction mixture. There the reaction is stirred at room temperature for at least 60 hours. Subsequently, the mixture is transferred to a separatory funnel and 0.5M HCl is added. The organic phase is removed and the aqueous phase extracted three times with 25 ml portions of diethyl ether. Combined organic layers are dried over anhydrous magnesium sulfate, filtered, and the solvent removed to yield an oil. The oil is dissolved in benzene and p-toluenesulfonic acid is added. The mixture is refluxed for 18 hours. Upon cooling to room temperature, water is added to the reaction vessel and the solution is transferred to a separatory funnel. The organic phase is removed and is extracted with 3 portions of benzene. The combined benzene layers are dried over anhydrous magnesium sulfate, filtered, and the solvent is removed to yield an oil. The oil is purified by column chromatography (silica gel 1:1 petroleum ether/methylene chloride). The oil contains the mixture of the Z and E-diastereomers of the ethene (Z/E-1-{4-[2,3,5,6-tetrafluoro-4-(trifluoromethyl) phenoxy]phenyl}-2-methyl-2-phenyl ethene).

II. Preparation of the Monomethyl Cyclopropane Intermediate (Z/E-1,1-dichloro-2-{4-[2,3,5,6-tetrafluoro-4-(trifluoromethyl) phenoxy]phenyl}-3-methyl-3-phenylcyclopropane)

A molar ratio (1:10) of triethylbenzylammonium chloride to the starting olefin from step I above (Z/E-1-{4-[2,3,5,6-tetrafluoro-4-(trifluoromethyl) phenoxy]phenyl}-2-methyl-2-phenyl ethene) is dissolved in excess chloroform (10 times the molar concentration of olefin) contained in a three neck flask fitted with an air condenser and dropping funnel. The flask is cooled in an ice water bath and a 33–50% aqueous sodium hydroxide solution (sodium hydroxide-chloroform, 2:1) is added dropwise while the mixture is magnetically stirred. After the addition is completed, the ice bath is removed and stirring continued for 120 hrs. The dark mixture is diluted with excess water and the aqueous layer is separated and extracted three times with chloroform. The chloroform extracts are combined, washed three times with water, dried over anhydrous magnesium sulfate, and filtered to remove the drying agent. The chloroform is removed under reduced pressure, yielding a dark liquid or solid which is purified by chromatography and recrystallization. The Z & E isomers are then separated by fractional crystallization. The diastereomers are readily identified by proton NMR spectroscopy.

III. Preparation of 3-Methyl Derivatives with Side Chains

To a solution of the Z isomer of the heptafluoro-tolyloxycyclopropane formed above (Z-1,1-dichloro-2-{4-[2,3,5,6-tetrafluoro-4-(trifluoromethyl) phenoxy]phenyl}-3-methyl-3-phenylcyclopropane) in dry N,N-dimethyl formamide is added sodium methoxide and the mixture is stirred at 40° C. for 2 hours. The mixture is then partitioned between diethyl ether and diluted sulfuric acid (0.05M). The ether layer is dried over anhydrous magnesium sulfate and concentrated. The crude phenol (compound without the heptafluorotolyl group) is dissolved in dry N,N-dimethylformamide under nitrogen, sodium hydride is added and the mixture is stirred and heated at 40° C. Then a side chain reagent (one of N,N-dimethylaminoethylchloride HCl salt; N,N-diethylaminoethylchloride HCl salt; 2-piperidinoethylchloride HCl salt; or 2-(N-methylpiperazino)ethylchloride HCl salt) is added in small portions over 30 minutes, and the mixture is maintained at 40° C. for an additional 30 minutes. Excess sodium hydride is destroyed by the addition of water and the resulting solution partitioned between ether and water. The aqueous layer is further extracted with ether, the combined ether solutions are dried over anhydrous magnesium sulfate and the solvent is evaporated. Chromatography of the residues give the respective desired side chain derivative of the 3-methyl cyclopropane compounds. Although it is preferred to use the Z isomer form of the intermediate, it will be readily apparent to one of ordinary skill in the art that the E isomer intermediate can also be used in the process thereby forming E isomer versions of the resulting products.

When N,N-dimethylaminoethylchloride HCl salt is used in Step III above as the side chain reagent a modified 3-methyl version of Compound 8, designated herein as Compound 8B and shown below, is formed:

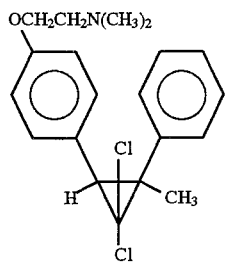

(Z)-1,1-Dichloro-2{4-[2-(dimethylamino)ethoxy]-
phenyl}-3-methyl-3-phenylcyclopropane
(Compound 8B)

When N,N-diethylaminoethylchloride HCl salt is used in Step III above as the side chain reagent a modified 3-methyl version of Compound 9, designated herein as Compound 9B and shown below, is formed:

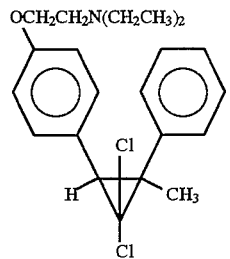

(Z)-1,1-Dichloro-2-{4-[2-diethylamino)ethoxy]-
phenyl}-3-methyl-3-phenylcyclopropane
(Compound 9B)

When 2-piperidinoethylchloride HCl salt is used in Step III above as the side chain reagent a modified 3-methyl version of Compound 10, designated herein as Compound 10B and shown below, is formed:

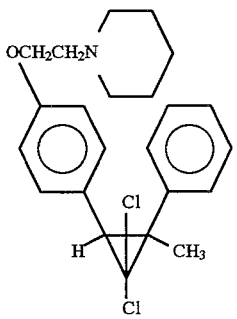

(Z)-1,1-Dichloro-2-{4-[2-(piperidino)ethoxy]-
phenyl}-3-methyl-3-phenylcyclopropane
(Compound 10B)

When 2-(N-methylpiperazino)ethylchloride HCl salt is used in Step III above as the side chain reagent a modified 3-methyl version of Compound 11, designated herein as Compound 11B and shown below, is formed:

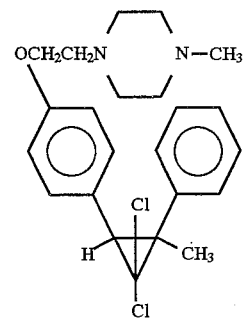

(Z)-1,1-Dichloro-2-{4-[2-(N-methylpiperazino)
ethoxy]-phenyl}-3-methyl-3-phenycyclopropane
(Compound 11B)

EXAMPLE 13

Preparation of 2,3-Dimethyl Compounds

I. Preparation of Starting Dimethyl Olefin (Z/E-1-{4-[2,3,5,6-tetrafluoro-4-(trifluoromethyl) phenoxy]phenyl}-1,2-dimethyl-2-phenyl ethene)

Figure 3A:
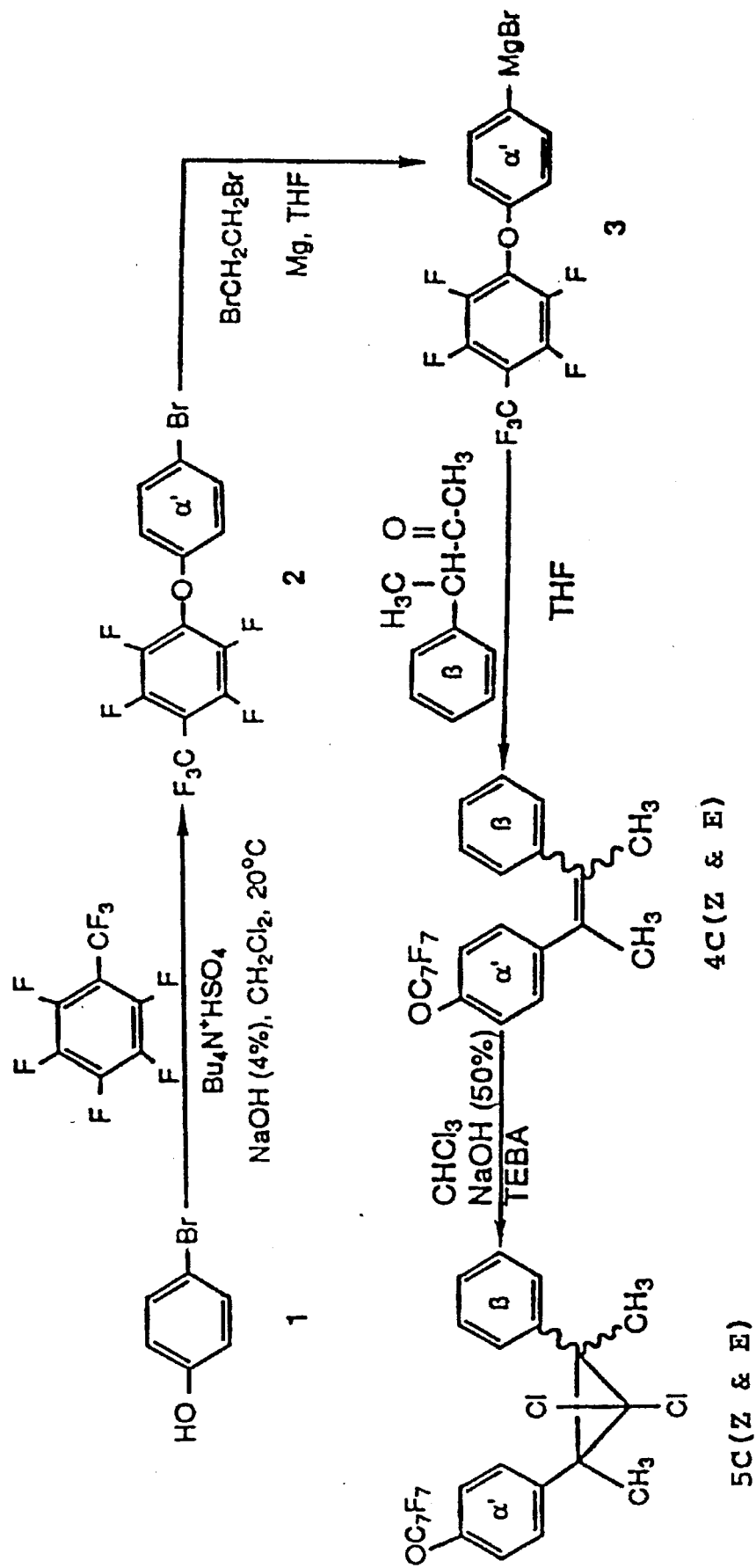
FIG. 3A is a portion of a scheme (Scheme III) showing a process for synthesizing four 2,3-dimethyl diphenylcyclopropanes, each having a different side chain.
Figure 3B:
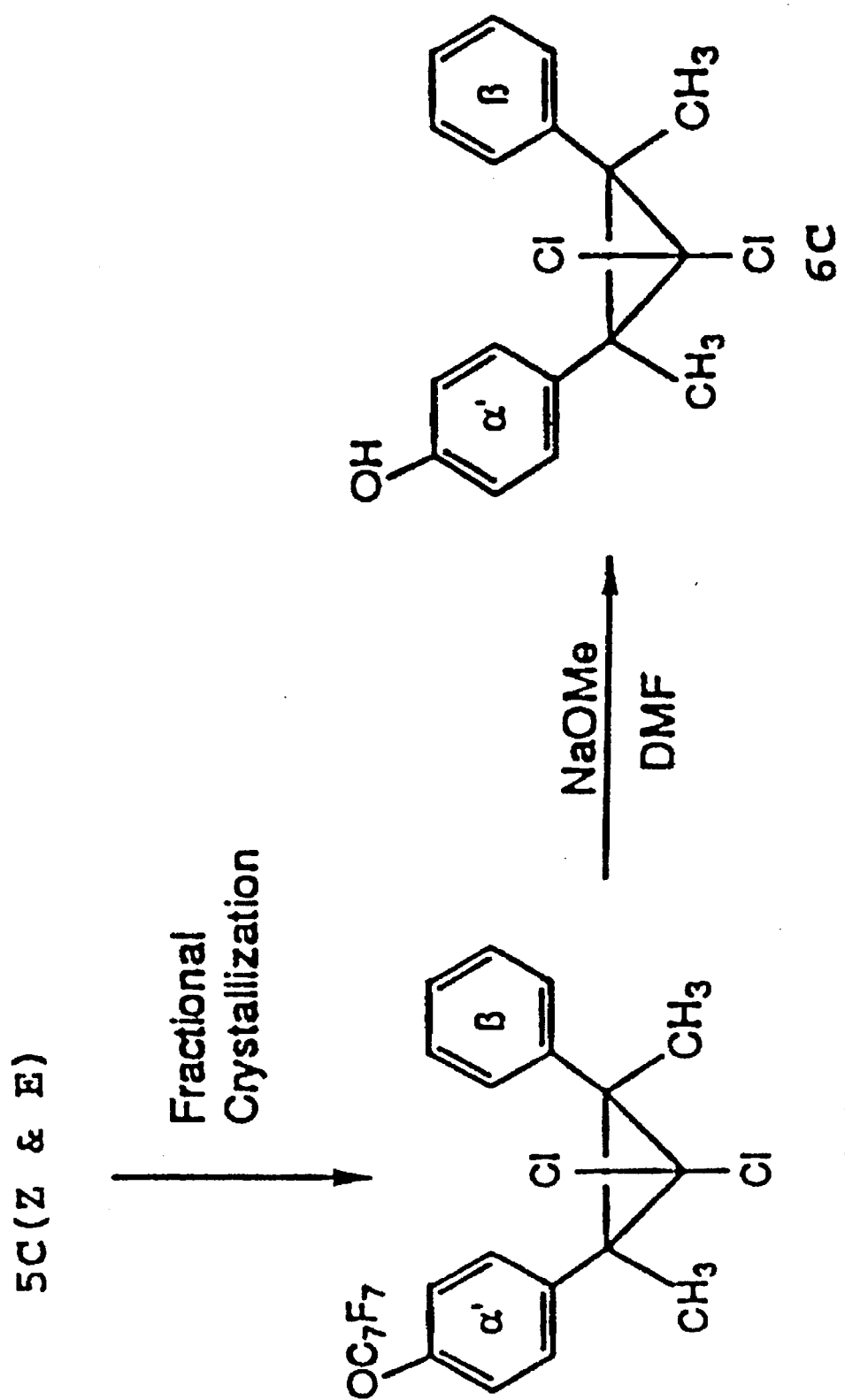
FIG. 3B is an intermediate portion of Scheme III.
Figure 3C:
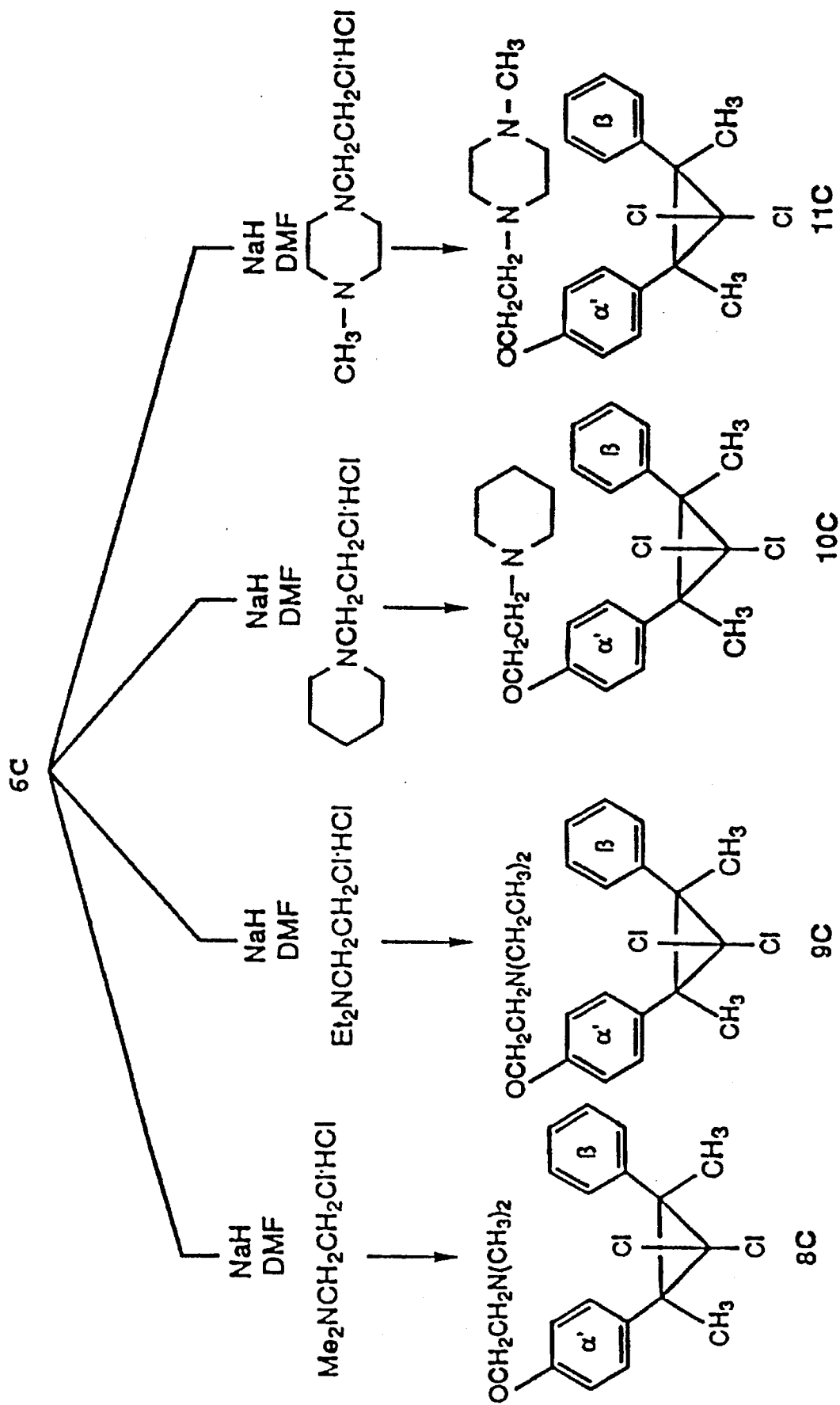
FIG. 3C is the final portion of Scheme III.

Preparation of four 2,3-dimethyl diphenylcyclopropanes (Compounds 8C-11C) is schematically shown in FIGS. 3A, 3B and 3C. To a flame-dried, three necked 500 ml round bottom flask equipped with a stir bar, reflux condenser, and pressure-equilibrating dropping funnel is added magnesium filings and 4-(perfluorotolyloxy) phenyl bromide (1:1.5) to freshly distilled THF (from Calcium Hydride). Dibromoethane dissolved in THF is then added slowly via the dropping funnel over several hours following the complete addition of dibromoethane and the disappearance of magnesium, α-methyl-α-phenyl acetone dissolved in THF is injected into the reaction mixture. There the reaction is stirred at room temperature for at least 60 hours. Subsequently, the mixture is transferred to a separatory funnel and 0.5M HCl is added. The organic phase is removed and the aqueous phase extracted three times with 25 ml portions of diethyl ether. Combined organic layers are dried over anhydrous magnesium sulfate, filtered, and the solvent removed to yield an oil. The oil is dissolved in benzene and toluenesulfonic acid is added. The mixture is refluxed for 18 hours. Upon cooling to room temperature, water is added to the reaction vessel and the solution is transferred to a separatory funnel. The organic phase is removed and is extracted with 3 portions of benzene. The combined benzene layers are dried over anhydrous magnesium sulfate, filtered, and the solvent is removed to yield an oil. The oil is purified by column chromatography (silica gel 1:1 petroleum ether/methylene chloride). The oil contains the mixture of the Z and E-diastereomers of the ethene (Z/E-1-{4-[2,3,5,6-tetrafluoro-4-(trifluoromethyl) phenoxy]phenyl}-1,2-dimethyl-2-phenyl ethene).

II. Preparation of the Monomethyl Cyclopropane Intermediate (Z/E-1,1-dichloro-2-{4-[2,3,5,6-tetrafluoro-4-(trifluoromethyl) phenoxy]phenyl}-2,3-dimethyl-3-phenylcyclopropane)

A molar ratio (1:10) of triethylbenzylammonium chloride to the starting olefin from step I above (Z/E-1-{4-[2,3,5,6-tetrafluoro-4-(trifluoromethyl) phenoxy]phenyl}-1,2-dimethyl-2-phenylethene) is dissolved in excess chloroform (10 times the molar concentration of olefin) contained in a three neck flask fitted with an air condenser and dropping funnel. The flask is cooled in an ice water bath and a 33-50% aqueous sodium hydroxide solution (sodium hydroxide-chloroform, 2:1) is added dropwise while the mixture is magnetically stirred. After the addition is completed, the ice bath is removed and stirring continued for 120 hrs. The dark mixture is diluted with excess water and the aqueous layer is separated and extracted three times with chloroform. The chloroform extracts are combined, washed three times with water, dried over anhydrous magnesium sulfate, and filtered to remove the drying agent. The chloroform is removed under reduced pressure, yielding a dark liquid or solid which is purified by chromatography and recrystallization. The Z & E isomers are then separated by fractional crystallization. The diastereomers are readily identified by protons spectroscopy.

III. Preparation of 2,3-Dimethyl Derivatives with Side Chains

To a solution of the Z isomer of the heptafluorotolyloxycyclopropane formed above (Z-1,1-dichloro-2-{4-[2,3,5,6-tetrafluoro-4-(trifluoromethyl) phenoxy]phenyl}-2,3-dimethyl-3-phenylcyclopropane) in dry N,N-dimethyl formamide is added sodium methoxide and the mixture is stirred at 40° C. for 2 hours. The mixture is then partitioned between diethyl ether and diluted sulfuric acid (0.05M). The ether layer is dried over anhydrous magnesium sulfate and concentrated. The crude phenol (compound without the heptafluorotolyl group) is dissolved in dry N,N-dimethylformamide under nitrogen, sodium hydride is added and the mixture is stirred and heated at 40° C. Then a side chain reagent (one of N,N-dimethylaminoethylchloride HCl salt; N,N-diethylaminoethylchloride HCl salt; 2-piperidinoethylchloride HCl salt; or 2-(N-methytpiperazino)ethylchloride HCl salt) is added in small portions over 30 minutes, and the mixture is maintained at 40° C. for an additional 30 minutes. Excess sodium hydride is destroyed by the addition of water and the resulting solution partitioned between ether and water. The aqueous layer is further extracted with ether, the combined ether solutions are dried over anhydrous magnesium sulfate and the solvent is evaporated. Chromatography of the residues give the respective desired side chain derivative of the 2,3-dimethyl cyclopropane compounds. Although it is preferred to use the Z isomer form of the intermediate, it will be readily apparent to one of ordinary skill in the art that the E isomer intermediate can also be used in the process to form isomer versions of the resulting products.

When N,N-dimethylaminoethylchloride HCl salt is used in Step III above as the side chain reagent a modified 2,3-dimethyl version of Compound 8, designated herein as Compound 8C and shown below, is formed:

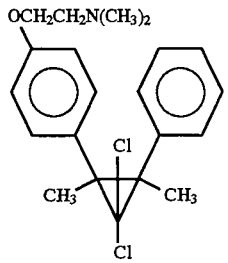

(Z)-1,1-Dichloro-2-{4-[2-(dimethylamino)ethoxy]-phenyl}-2,3-dimethyl-3-phenylcyclopropane (Compound 8C)

When N,N-diethylaminoethylchloride HCl salt is used in Step III above as the side chain reagent a modified 2,3-dimethyl version of Compound 9, designated herein as Compound 9C and shown below, is formed:

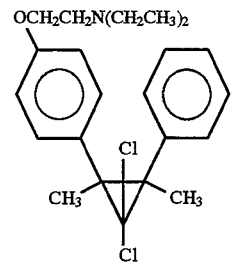

(Z)-1,1-Dichloro-2-{4-[2-(diethylamino) ethoxy]-phenyl}-2,3-dimethyl -3-phenylcyclopropane (Compound 9C)

When 2-piperidinoethylchloride HCl salt is used in Step III above as the side chain reagent a modified 2,3-dimethyl version of Compound 10, designated herein as Compound 10C and shown below, is formed:

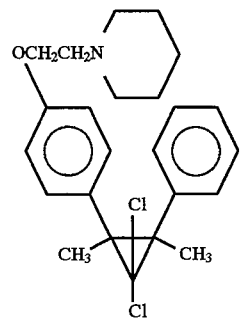

(Z)-1,1-Dichloro-2-{4-[2-(piperidino)ethoxy]-phenyl}-2,3-dimethyl-3-phenylcyclopropane (Compound 10C)

When 2-(N-methylpiperazino)ethylchloride HCl salt is used in Step III above as the side chain reagent a modified 2,3-dimethyl version of Compound 11, designated herein as Compound 11C and shown below, is formed:

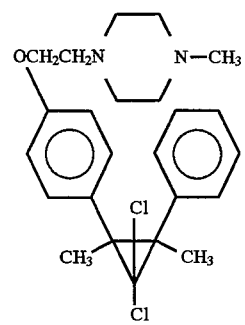

(Z)-1,1-Dichloro-2-{4-[2-(N-methylpiperazino) ethoxy]-phenyl}-2,3-dimethyl -3-phenylcyclopropane (Compound 11C)

EXAMPLE 14

Biological Testing

The biological evaluation of the diphenylcyclopropanes having substituted alkoxy side chains (compounds 7, 8, 9, 10 and 11) consisted of the in vitro rat cytosolic estradiol receptor binding assay, the in vivo immature mouse uterotrophic (estrogenic) assay, and the in vivo immature mouse and rat antiuterotropic (antiestrogenic) assay and in the in vitro suppression of the proliferation of the MCF-7 human breast cancer cell line. All assays contained estradiol, TAM, MER 25, and 1-1-dichloro-2-3-cis-diphenylcyclopropane (Analog II) as standards.

Biological Assays. Tamoxifen was obtained from Stuart Pharmaceutical, Division of ICI Americas, Inc., Wilmington, Del. MER 25 was obtained from Merrell Dow Research Institute, Division of Merrell Dow Pharmaceuticals, Inc., Cincinnati, Ohio. Absolute ethanol was obtained from U.S. Industrial Chemicals Co. Hormones and biochemicals were purchased from Sigma Chemical Co. Animals and Housing. Viral-free immature female Swiss-Webster mice were obtained at 17–19 days of age from Sasco (Omaha, Nebraska) weighing 8–10 g, and were used in the uterotropic and antiuterotropic assays. Immature female Sprague-Dawley rats, obtained also at 17–19 days of age from Sasco, weighing 28–33 g, were used in the estradiol receptor binding assay. Animals were housed in wire topped polycarbonate cages with six animals per cage. Environment was controlled at 25 ° C. with a 12-hour light/dark cycle. The animals received a diet of Wayne Lab Blox rodent chow and tab water ad libitum.

EXAMPLE 15

Uterotropic Assay

Estrogenic activity of compounds 7–11 was determined using a modification of the method of Rubin, B. L., et al., *Endocrinology* 49:429 (1951) (see Pento, J. T., et al.;l *J. Endocrinol.* 61:1216 (1978)) using immature (17–19 days old) female Swiss-Webster mice. The test compounds were dissolved separately in a minimum amount of isopropyl myristate (IPM), and diluted serially with sesame oil to the proper concentrations (final concentration of IPM <5%). Solutions were shaken at 25° C. for several hours to ensure complete dissolution. The mice were randomly separated into groups of six animals, weighed, and the compounds were administered by s.c. injection of 0.1 mL of the oil solutions into the nape of the neck for 3 consecutive days. The solutions were periodically checked by TLC to insure homogeneity. A control group received 0.1 mL sesame oil alone.

The animals were anesthetized with $Et_2O$ and sacrificed by cervical dislocation 24 h after the last injection. Body weights were determined and the uteri were removed, cleaned of adhering connective tissue and fat, blotted to remove tissue fluid, and weighed to the nearest 0.1 mg.

The compounds shown in Table VII, with the exception of compound 11, did not produce any uterotropic activity in the immature mouse at doses of 30, 150, and 750 μg. Compounds 7, 8, 9 and 10 caused a reduction in uterine weight as compared with MER-25 which produced estrogenic responses at the 150 and 750 μg doses.

TABLE VII (Z)-1,1-Dichloro-2,3-Diarylcyclopropane Derivatives

| Compound No. | R | Formula |
|---|---|---|
| 7 | $OSO_2CH_3$ | $C_{18}H_{18}Cl_2SO_4$ |
| 8 | $N(CH_3)_2$ | $C_{19}H_{21}Cl_2NO$ |
| 9 | $N(CH_2CH_3)_2$ | $C_{21}H_{25}Cl_2NO$ |

TABLE VII-continued (Z)-1,1-Dichloro-2,3-Diarylcyclopropane Derivatives

| Compound No. | R | Formula |
|---|---|---|
| 10 | $c-NC_5H_{10}$ | $C_{22}H_{25}Cl_2NO$ |
| 11 | $c-N(CH_2CH_2)_2N-CH_3$ | $C_{22}H_{26}Cl_2NO$ |

EXAMPLE 16

Antiuterotropic Assay

Antiestrogenic activity of the compounds was determined by inhibition of the estradiol-induced uterotropic activity in immature female Swiss-Webster mice. Animals were distributed into groups of six animals. Estradiol was dissolved in sesame oil (0.1 μg/mL). The test compounds were dissolved in IPM and diluted with IPM to achieve desired concentrations. The solutions were periodically checked by TLC to insure homogeneity. Injections were made in the nape of the neck for 3. consecutive days. The unstimulated control group received vehicles alone (0.05 mL IPM and 0.1 mL sesame oil each day), while the stimulated control group received 0.1 mL of the estradiol solution (total dose 0.03 All test groups received 0.1 mL of the stimulating dose of estradiol (0.01 μg) plus 0.05 mL of the test compounds solutions each day. The IPM and oil injections were made at separate sites to minimize possible physical or chemical interactions or reduced absorption of either compound. Antiestrogenic activity was measured as a decrease from the estradiol-induced increase in uterine weight seen in the test compound groups versus the estradiol-stimulated group alone.

A series of side-chain derivatives of the antiestrogen, Analog II and MER 25 were examined for estrogen antagonism at doses of 30, 150 and 750 μg against a stimulating dose of 0.03 μg of estradiol.

Compounds 8, 9, 10 and 11 produced some antiestrogenic activity, while compound 7 did not (Table VIII). Compound 9 induced an antiestrogen response of 39.7% as compared to 37.1% of Analog II at 30 and 750 μg dosages respectively. The compounds in Table VII did not produce any significant decrease in uterine weight at the highest dose of 750 μg but elicited antiestrogenic activity at the lower doses of 30 and 150 μg.

Analog II and MER 25 produced a dose dependent decrease in uterine weight, with MER 25 eliciting the highest observed antiestrogenic activity of 66%. None of the compounds potentiated the uterine weight gain from the stimulating dose of.0.03 μg of estradiol.

TABLE VIII

OBSERVED ANTIESTROGENIC ACTIVITIES[a]

| Compound | Total Dose (μg) | % Observed Antiestrogenic Activity[aa] |
|---|---|---|
| 7 | 30 | 7.23 |
|   | 150 | — |
|   | 750 | — |
| 8 | 30 | 9.26 |
|   | 150 | 25.20 |
|   | 750 | 11.25 |
| 9 | 30 | 39.70 |
|   | 150 | 22.44 |

TABLE VIII-continued

OBSERVED ANTIESTROGENIC ACTIVITIES[a]

| Compound | Total Dose (µg) | % Observed Antiestrogenic Activity[aa] |
|---|---|---|
|  | 750 | 15.50 |
| 10 | 30 | 28.41 |
|  | 150 | 33.87 |
|  | 750 | 27.79 |
| 11 | 30 | 10.15 |
|  | 150 | 32.10 |
|  | 750 | 17.53 |
| Analog II | 30 | 24.65 |
|  | 150 | 31.96 |
|  | 750 | 37.12 |
| MER-25 | 30 | 24.46 |
|  | 150 | 24.17 |
|  | 750 | 66.42 |

[a]Determined as the decrease in the estradiol-stimulated (0.03 µg total dose) uterine wt. of immature female mice.
[aa]Calculated by: {(mean uterine wt. of estradiol-stimulated − mean uterine wt. of control) − (mean uterine wt. of test compounds − mean uterine wt. of control)/(mean uterine wt. of estradiol-stimulated − mean uterine wt. of control)} × 100.

EXAMPLE 17

Receptor Binding Assay

The receptor binding activities of the test compounds for the estrogenic receptors were determined by displacement of [$^3$H]-estradiol from rat uterine cytosol in vitro. Female Sprague-Dawley rats (17–19 days old) were treated with 0.53 µg of estradiol in 0.1 mL sesame oil for three consecutive days (total dose 1.6 µg). On the fourth day the rats were anesthetized with $Et_2O$ and sacrificed by cervical dislocation. A modification of Korenman's receptor binding assay method (Korenman, S. G., Steroids 13:163 (1969)) was used. Uteri were removed, cleaned of adhering connective tissue and fat, weighed (avg. wt.=83 mg/animal), and homogenized (Polytron PT-10 stainless steel homogenizer, rheostat setting 7, five ten-second bursts with a ten-second pause between bursts) at 0–4 °C. in five volumes (w/v) of TEDM buffer (10 mM Tris-HCl, 1.5 mM disodium ethylenediamine tetraacetic acid, 1.0 mM dithiothreitol, 10.0 mM sodium molybdate, pH adjusted to 7.4 with 5M NaOH). The resulting homogenate was centrifuged at 2000 g for 15 min (4° C.). The supernatant was then centrifuged at 104,000 g for 1 h (4° C.). The supernatant from the high speed centrifugation (cytosol) was carefully decanted and used immediately. The protein content of the cytosol was determined and adjusted to 4–5 mg protein/mL. The test compounds were dissolved in EtOH or DMSO and diluted with TEDM so that the final EtOH concentration was less than 2% or the final DMSO concentration was less than 10%. Neither of these concentrations of the organic solvents affected the binding of the tritiated estradiol to the cytosolic receptor or the amount of non-specific binding seen as determined by parallel incubations. Duplicate incubations were conducted at 4° C. for 24 h in a total volume of 0.5 mL containing: 200 µL cytosol; 100 µL (0.218 µCi) of 2,4,6,7(n)-[$^3$H]-17β-estradiol (93.35 mCi/mmole); 100 µL of the test compounds at concentrations ranging from $10^{-4}$ to $10^{-6}$M, or unlabelled estradiol at concentrations ranging from $10^{-6}$ to $10^{-8}$M; and sufficient TEDM to obtain a final volume of 0.5 mL. Single parallel incubations at each concentration of test compound and estradiol contained 100 µL of $2\times10^{-3}$M DES in the final TEDM addition to distinguish between specific receptor binding and non-specific protein/receptor binding of the compounds.

After incubation, 0.5 mL of a Dextran-Coated Charcoal (DCC) solution (0.5% activated charcoal and 0.05% Dextran T-70, w/v, in TEDM buffer) was added and the tubes were gently vortexed at 4° C. 15 min. The tubes were centrifuged at 2000 g 15 min (4° C.) to remove the unbound [$^3$H]-estradiol. A 0.5 mL aliquot of the supernatant was added to 10 mL Beckmann Ready-Solv VI scintillation cocktail in subdued light and the tritium content of each vial was determined by liquid scintillation spectrometry. The radioactivity was plotted as a function of the log concentration of competing ligand and subjected to linear regression analysis. Relative binding affinity of each compound was determined by the method of Bliss, C. I., The Statistics of Bioassay, Academic Press (New York 1952).

The compounds in Table VII produced no displacement of [$^3$H]-estradiol from the rat uterine cytosol, while tamoxifen and Analog II produced a parallel displacement with estradiol indicating a relative binding affinity for the ER. Both the free bases and the citrate salts of the compounds were tested in the ER binding assay.

EXAMPLE 18

Statistical Analysis

The relative binding affinity determinations were performed by a TI-59 programmable calculator (Texas Instruments). The Student's t-test (non-paired) was used to compare individual treatment groups to the estradiol group statistically. Multiple group comparison were analyzed by ANOVA. P or F values of less than 0.05 were considered to be significant. The Student's t values, ANOVA F values, linear regression and standard errors were obtained by Cricket Graph and StatWorks programs on a Macintosh computer.

EXAMPLE 19

The compounds shown in Table VII Were found to be devoid of estrogenic activity, but possessed a small degree of antiestrogenic activity in the mouse. These compounds produced a 10 to 37% decrease in estradiol-stimulated uterotropic activity at the doses tested (see Table VIII). None of the cyclopropyl side-chain compounds (Table VII) displaced [$^3$H]-estradiol from the ER in the rat uterine cytosol as determined by the competitive binding assay. Since it is known that there is a correlation between ER binding affinity and estrogenic activity, it can be assumed from the receptor binding data that the compounds, which were poor binders, lacked estrogenic activity. As observed in the uterotrophic assay, none of the compounds (Table VII) increased uterine weight as compared to the non-treated control group and they did not potentiate the uterotropic response of the stimulating dose of estradiol in the antiuterotropic assay, clearly indicating that the compounds are not estrogenic in the mouse. Analog II and MER-25 used as standards, elicited a significant decrease in uterine weight only at the highest tested dose of 750 µg.

EXAMPLE 20

In Vitro testing of MCF-7, Human Breast Cell Cancer Line

MCF-7 Cell Culture Method. MCF-7 human breast cancer cells were obtained from the Michigan Cancer Foundation. MCF-7 cells were grown at 37° C. in 75 $cm^2$ tissue culture (T-75) flasks, as monolayer cultures in RPMI 1640 media (without phenol red) supplemented with 2 mM 1-glutamine, gentamicin (50 μg/mL), penicillin (100 units/mL), streptomycin (100 μg/mL) and calf serum (5%). Cultures were grown in an incubator at 37° C. in a humid 5% $CO_2$ atmosphere, and fed on alternate days. Exponential growth was maintained by subculturing at eight day intervals when the cell number per T-75 flask reached 10 to $12 \times 10^6$ cells.

All of the compounds were tested for their ability to alter the growth of MCF-7 cells at a concentration ranging from $10^{-4}$ to $10^{-6}$ M. Growth inhibition produced at concentrations greater than $5 \times 10^{-6}$ M are considered to be cytotoxic anti-tumor effects. Control samples received vehicle alone at the same concentrations used in the treatment groups.

In each experiment, the cells were trypsinized, washed and plated in multiwell plates at a density of $5 \times 10^4$ cells/well in 3 mL of RPMI 1640 media. Cells were allowed to attach and were in logarithmic growth when the test compounds were added. Each group was done in triplicate. The test compounds were dissolved in a polyethylene glycol 400:ethanol (55:45) mixture and added in the culture media. The final concentration of the vehicle mixture was 0.1% of the incubation media. Cell growth was measured on alternate days using the hemocytometric trypan blue exclusion method.

Statistics. The student's t-test (non-paired) was used to make statistical comparisons between two experimental groups. Multiple group comparisons in the cell culture experiments were made using a 3-way ANOVA. P values of less than 0.05 were considered to be statistically significant. The student's t values, standard errors, and linear regression were obtained using the Stat Work and Cricket Graph programs on a Macintosh computer.

Results. The results of the MCF-7 human breast cancer cell culture study indicate that compound 10 abolished cell growth at $10^{-4}$ M (Table IX), significantly reduced cell growth at $10^{-5}$ M (Table X), and had no effect on cell growth at $10^{-6}$ M (Table XI). These data indicate that compound 10 is cytotoxic to human breast cancer cells in culture. Cell growth was inhibited by tamoxifen (a known antiestrogen) at a concentration of $10^{-6}$ M confirming the estrogen-specific nature of the MCF-7 cell used in this study.

TABLE IX

Effect of $10^{-4}$ M Compound 10 on Cell Growth

| | Mean Live Cell Count Per Well | | |
|---|---|---|---|
| Days | Control | Compound 10, $10^{-4}$ M | Tamoxifen, $10^{-6}$ M |
| 0 | 81,481 | 81,481 | — |
| 2 | 158,333 | — | — |
| 4 | 256,944 | 5,324 | — |
| 6 | 235,417 | 1,620 | — |

TABLE X

Effect of $10^{-5}$ M Compound 10 on Cell Growth

| | Mean Live Cell Count Per Well | | |
|---|---|---|---|
| Days | Control | Compound 10, $10^{-5}$ M | Tamoxifen, $10^{-6}$ M |
| 0 | 118,056 | 118,056 | 118,056 |
| 2 | 227,315 | 115,741 | 248,611 |
| 4 | 474,074 | 186,111 | 332,407 |
| 6 | 648,148 | 50,000 | 547,222 |

TABLE XI

Effect of $10^{-6}$ M Compound 10 on Cell Growth

| | Mean Live Cell Count Per Well | | |
|---|---|---|---|
| Days | Control | Compound 10, $10^{-6}$ M | Tamoxifen, $10^{-6}$ M |
| 0 | 91,204 | 91,204 | 91,204 |
| 2 | 149,537 | 215,278 | 105,093 |
| 4 | 415,741 | 430,556 | 387,963 |
| 6 | 526,389 | 537,037 | 647,222 |

All U. S. patent applications and publications cited herein are hereby incorporated by reference.

Changes may be made in the embodiments of the invention described herein or in parts or elements of the embodiments described herein or in the steps or in the sequence of steps of the methods described herein without departing from the spirit and scope of the invention as defined in the following claims.

What is claimed is:

1. A compound having the formula:

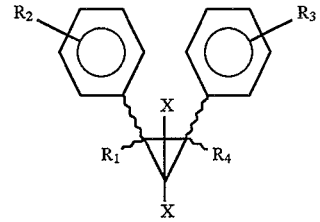

or any pharmaceutically acceptable salt thereof, in which:

X is a hydrogen or halogen atom;

$R_1$ is a hydrogen atom or an alkyl group containing from 1 to 3 carbon atoms;

$R_2$ is selected from the group consisting of,
  a hydrogen atom, and
  a substituted alkoxy group in which the substituent of the alkoxy group is selected from a group consisting of,
    a dialkylamino group in which the alkyl substituent contains from 1 to 6 carbon atoms, and
    an alkylsulfonyloxy group in which the alkyl substituent contains from 1 to 6 carbon atoms $R_3$ is selected from the group consisting of,
  a hydrogen atom, and
  a substituted alkoxy group in which the substituent of the alkoxy group is selected from a group consisting of,
    a dialkylamino group in which the alkyl substituent contains from 1 to 6 carbon atoms, and
    an alkylsulfonyloxy group in which the alkyl substituent contains from 1 to 6 carbon atoms; and $R_4$ is a hydrogen atom or an alkyl group containing from 1 to 3 carbon atoms; and with the proviso that $R_1$ and $R_4$ cannot simultaneously be hydrogen, and further with the proviso that $R_2$ and $R_3$ cannot simultaneously be hydrogen and wherein the bonds designated by (∼)

represent that the compound can be in the cis- or trans-isomer configuration.

2. The composition of claim 1 in which $R_2$ is selected from a group consisting of:

a dialkylaminoalkoxy group, and an alkylsulfonyloxy alkoxy group.

3. The compound of claim 2 wherein at least one of $R_1$ and $R_4$ is a methyl group.

4. The compound of claim 3 wherein $R_1$ and $R_4$ are methyl groups.

5. The compound of claim 4 wherein the $R_3$ is hydrogen.

6. The compound of claim 5 wherein the $R_2$ group is in the para ring position.

7. The composition of claim 1 in which $R_3$ is selected from a group consisting of:

a dialkylaminoalkoxy group, and an alkylsulfonyloxy alkoxy group.

8. The compound of claim 7 wherein at least one of $R_1$ and $R_4$ is a methyl group.

9. The compound of claim 8 wherein $R_1$ and $R_4$ are methyl groups.

10. The compound of claim 9 wherein the $R_2$ is hydrogen.

11. The compound of claim 10 wherein the $R_3$ group is in the para ring position.

12. The compound of claim 1 wherein the X is a chlorine atom.

13. A compound having the formula:

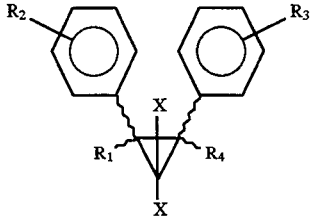

or any pharmaceutically acceptable salt thereof, in which:

X is a hydrogen or halogen atom;

$R_1$ is a hydrogen atom or a methyl group;

$R_2$ is selected from the group consisting of, a hydrogen atom, and a substituted alkoxy group in which the substituent of the alkoxy group is selected from a group consisting of, a dialkylamino group in which the alkyl substituent contains from 1 to 6 carbon atoms, and an alkylsulfonyloxy group in which the alkyl substituent contains from 1 to 6 carbon atoms;

$R_3$ is selected from the group consisting of, a hydrogen atom, and a substituted alkoxy group in which the substituent of the alkoxy group is selected from a group consisting of, a dialkylamino group in which the alkyl substituent contains from 1 to 6 carbon atoms, and an alkylsulfonyloxy group in which the alkyl substituent contains from 1 to 6 carbon atoms; and $R_4$ is a hydrogen atom or a methyl group; and with the proviso that $R_1$ and $R_4$ cannot simultaneously be hydrogen, and further with the proviso that $R_2$ and $R_3$ cannot simultaneously be hydrogen and wherein the bonds designated by ($\sim$)

represent that the compound can be in the cis- or trans- isomer configuration.

14. The composition of claim 13 in which $R_2$ is selected from a group consisting of:

a dialkylaminoalkoxy group, and an alkylsulfonyloxy alkoxy group.

15. The compound of claim 14 wherein $R_m$ and $R_1$ are methyl groups.

16. The compound of claim 15 wherein the $R_3$ is hydrogen.

17. The compound of claim 16 wherein the $R_2$ group is in the para ring position.

18. The composition of claim 13 in which $R_2$ is selected from a group consisting of:

a dialkylaminoalkoxy group, and an alkylsulfonyloxy alkoxy group.

19. The compound of claim 18 wherein $R^1$ and $R_4$ are methyl groups.

20. The compound of claim 19 wherein the $R_3$ is hydrogen.

21. The compound of claim 20 wherein the $R_2$ group is in the para ring position.

22. The compound of claim 13 wherein the X is a chlorine atom.

23. A composition of matter comprising: a compound having the formula:

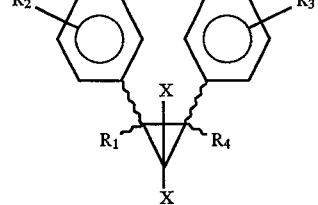

or any pharmaceutically acceptable salt thereof, in which:

X is a hydrogen or halogen atom;

$R_1$ is a hydrogen atom or an alkyl group containing from 1 to 3 carbon atoms;

$R_1$ is selected from the group consisting of, a hydrogen atom, and a substituted alkoxy group in which the substituent of the alkoxy group is selected from a group consisting of, a dialkylamino group in which the alkyl substituent contains from 1 to 6 carbon atoms, and an alkylsulfonyloxy group in which the alkyl substituent contains from 1 to 6 carbon atoms;

$R_3$ is selected from the group consisting of, a hydrogen atom, and a substituted alkoxy group in which the substituent of the alkoxy group is selected from a group consisting of, a dialkylamino group in which the alkyl substituent contains from 1 to 6 carbon atoms, and an alkylsulfonyloxy group in which the alkyl substituent contains from 1 to 6 carbon atoms; and $R_4$ is a hydrogen atom or an alkyl group containing from 1 to 3 carbon atoms; and with the proviso that $R_1$ and $R_1$ cannot simultaneously be hydrogen, and further with the proviso that $R_2$ and $R_3$ cannot simultaneously be hydrogen and wherein the bonds designated by (∼)

represent that the compound can be in the cis- or trans-isomer configuration; and a pharmaceutically acceptable carrier of sufficient quantity to solubilize the compound.

24. The composition of claim 23 in which $R_2$ is selected from a group consisting of:
a dialkylaminoalkoxy group, and
an alkylsulfonyloxy alkoxy group.

25. The composition of claim 24 wherein at least one of $R_1$ and $R_4$ is a methyl group.

26. The composition of claim 25 wherein $R_1$ and $R_4$ are methyl groups.

27. The composition of claim 26 wherein the $R_3$ is hydrogen.

28. The composition of claim 27 wherein the $R_2$ group is in the para ring position.

29. The composition of claim 23 in which $R_3$ is selected from a group consisting of:
a dialkylaminoalkoxy group, and
an alkylsulfonyloxy alkoxy group.

30. The composition of claim 29 wherein at least one of $R_1$ and $R_4$ is a methyl group.

31. The composition of claim 30 wherein $R_1$ and $R_4$ are methyl groups.

32. The composition of claim 31 wherein the $R_2$ is hydrogen.

33. The composition of claim 32 wherein the $R_1$ group is in the para ring position.

34. The composition of claim 23 wherein the X is a chlorine atom.

35. A composition of matter comprising:
a compound having the formula:

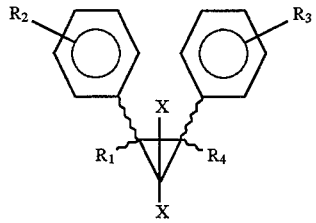

or any pharmaceutically acceptable salt thereof, in which:
X is a hydrogen or halogen atom;
$R^1$ is a hydrogen atom or a methyl group;
$R_2$ is selected from the group consisting of,
a hydrogen atom, and
a substituted alkoxy group in which the substituent of the alkoxy group is selected from a group consisting of,
a dialkylamino group in which the alkyl substituent contains from 1 to 6 carbon atoms, and
an alkylsulfonyloxy group in which the alkyl substituent contains from 1 to 6 carbon atoms;
$R_3$ is selected from the group consisting of,
a hydrogen atom, and
a substituted alkoxy group in which the substituent of the alkoxy group is selected from a group consisting of, a dialkylamino group in which the alkyl substituent contains from 1 to 6 carbon atoms, and
an alkylsulfonyloxy group in which the alkyl substituent contains from 1 to 6 carbon atoms; and
$R_4$ is a hydrogen atom or a methyl group; and
with the proviso that $R_1$ and $R_4$ cannot simultaneously be hydrogen, and further with the proviso that $R_2$ and $R_3$ cannot simultaneously be hydrogen and wherein the bonds designated by (∼)

represent that the compound can be in the cis- or trans-isomer configuration; and a pharmaceutically acceptable carrier of sufficient quantity to solubilize the compound.

36. The composition of claim 35 in which $R_2$ is selected from a group consisting of:
a dialkylaminoalkoxy group, and
an alkylsulfonyloxy alkoxy group.

37. The composition of claim 36 wherein $R^1$ and $R_4$ are methyl groups.

38. The composition of claim 37 wherein the $R_3$ is hydrogen.

39. The composition of claim 38 wherein the $R_2$ group is in the para ring position.

40. The composition claim 35 in which $R_3$ is selected from a group consisting of:
a dialkylaminoalkoxy group, and
an alkylsulfonyloxy alkoxy group.

41. The composition of claim 40 wherein $R^1$ and $R_4$ are methyl groups.

42. The composition of claim 41 wherein the $R^2$ is hydrogen.

43. The composition of claim 42 wherein the $R_3$ group is in the para ring position.

44. The compound of claim 35 wherein the X is a chlorine atom.

45. A method of inducing antiestrogenic activity in a mammal in need of such therapy, comprising:
administering to the mammal an antiestrogenically effective amount of one or more of the compounds having the formula:

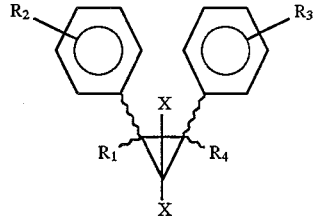

or any pharmaceutically acceptable salt thereof, in which:
X is a hydrogen or halogen atom;
$R_1$ is a hydrogen atom or an alkyl group containing from 1 to 3 carbon atoms;
$R_2$ is selected from the group consisting of,
a hydrogen atom, and
a substituted alkoxy group in which the substituent of the alkoxy group is selected from a group consisting of,
a dialkylamino group in which the alkyl substituent contains from 1 to 6 carbon atoms; and an alkylsulfonyloxy group in which the alkyl substituent contains from 1 to 6 carbon atoms;

$R_3$ is selected from the group consisting of,
   a hydrogen atom, and
   a substituted alkoxy group in which the substituent of the alkoxy group is selected from a group consisting of,
      a dialkylamino group in which the alkyl substituent contains from 1 to 6 carbon atoms, and
      an alkylsulfonyloxy group in which the alkyl substituent contains from 1 to 6 carbon atoms; and $R_4$ is a hydrogen atom or an alkyl group containing from 1 to 3 carbon atoms; and with the proviso that $R_1$ and $R_4$ cannot simultaneously be hydrogen, and further with the proviso that $R_2$ and $R_3$ cannot simultaneously be hydrogen and wherein the bonds designated by $$(\sim)$$

represent that the compound can be in the cis- or trans-isomer configuration.

46. The method of claim 45 in which $R_2$ is selected from a group consisting of:
   a dialkylaminoalkoxy group, and
   an alkylsulfonyloxy alkoxy group.

47. The method of claim 46 wherein at least one of $R_1$ and $R_4$ is a methyl group.

48. The method of claim 47 wherein $R_1$ and $R_4$ are methyl groups.

49. The method of claim 48 wherein the $R_3$ is hydrogen.

50. The method of claim 49 wherein the $R_2$ group is in the para ring position.

51. The method of claim 45 in which $R_3$ is selected from a group consisting of:
   a dialkylaminoalkoxy group, and
   an alkylsulfonyloxy alkoxy group.

52. The method of claim 51 wherein at least one of $R_1$ and $R_4$ is a methyl group.

53. The method of claim 52 wherein $R_1$ and $R_4$ are methyl groups.

54. The method of claim 53 wherein the $R_2$ is hydrogen.

55. The method of claim 54 wherein the $R_3$ group is in the para ring position.

56. The method of claim 45 wherein the X is a chlorine atom.

57. A method of inducing antiestrogenic activity in a mammal in need of such therapy, comprising:
   administering to the mammal an antiestrogenically effective amount of one or more of the compounds having the formula:

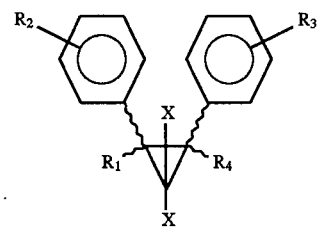

or any pharmaceutically acceptable salt thereof, in which:
   X is a hydrogen or halogen atom;
   $R^1$ is a hydrogen atom or a methyl group;

$R_2$ is selected from the group consisting of,
   a hydrogen atom, and
   a substituted alkoxy group in which the substituent of the alkoxy group is selected from a group consisting of,
      a dialkylamino group in which the alkyl substituent contains from 1 to 6 carbon atoms, and
      an alkylsulfonyloxy group in which the alkyl substituent contains from 1 to 6 carbon atoms;

$R_3$ is selected from the group consisting of,
   a hydrogen atom, and
   a substituted alkoxy group in which the substituent of the alkoxy group is selected from a group consisting of,
      a dialkylamino group in which the alkyl substituent contains from 1 to 6 carbon atoms, and
      an alkylsulfonyloxy group in which the alkyl substituent contains from 1 to 6 carbon atoms; and $R_4$ is a hydrogen atom or a methyl group; and with the proviso that $R^1$ and $R_4$ cannot simultaneously be hydrogen, and further with the proviso that $R_2$ and $R_3$ cannot simultaneously be hydrogen and wherein the bonds designated by $$(\sim)$$

represent that the compound can be in the cis- or trans-isomer configuration.

58. The method of claim 57 in which $R_2$ is selected from a group consisting of:
   a dialkylaminoalkoxy group, and
   an alkylsulfonyloxy alkoxy group.

59. The method of claim 58 wherein $R^1$ and $R_4$ are methyl groups.

60. The method of claim 59 wherein the $R_3$ is hydrogen.

61. The method of claim 60 wherein the $R_2$ group is in the para ring position.

62. The method of claim 57 in which $R_3$ is selected from a group consisting of:
   a dialkylaminoalkoxy group, and
   an alkylsulfonyloxy alkoxy group.

63. The method of claim 62 wherein $R_1$ and $R_4$ are methyl groups.

64. The method of claim 62 wherein the $R_2$ is hydrogen.

65. The method of claim 64 wherein the $R_3$ group is in the para ring position.

66. The method of claim 57 wherein the X is a chlorine atom.

67. A method of inhibiting the development of an estrogen-dependent tumor in a mammal in need of such therapy, comprising:
   administering to the mammal an effective amount of one or more of the compounds having the formula:

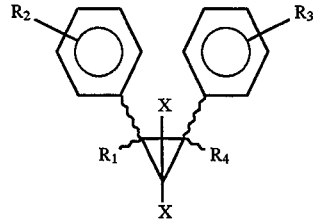

or any pharmaceutically acceptable salt thereof, in which:

X is a hydrogen or halogen atom;

$R_1$ is a hydrogen atom or an alkyl group containing from 1 to 3 carbon atoms;

$R_2$ is selected from the group consisting of,
  a hydrogen atom, and
  a substituted alkoxy group in which the substituent of the alkoxy group is selected from a group consisting of,
    a dialkylamino group in which the alkyl substituent contains from 1 to 6 carbon atoms, and
    an alkylsulfonyloxy group in which the alkyl substituent contains from 1 to 6 carbon atoms;

$R_3$ is selected from the group consisting of,
  a hydrogen atom, and
  a substituted alkoxy group in which the substituent of the alkoxy group is selected from a group consisting of,
    a dialkylamino group in which the alkyl substituent contains from 1 to 6 carbon atoms, and
    an alkylsulfonyloxy group in which the alkyl substituent contains from 1 to 6 carbon atoms; and $R_4$ is a hydrogen atom or an alkyl group containing from 1 to 3 carbon atoms; and with the proviso that $R_1$ and $R_4$ cannot simultaneously be hydrogen, and further with the proviso that $R_2$ and $R_1$ cannot simultaneously be hydrogen and wherein the bonds designated by ($\sim$)

represent that the compound can be in the cis- or trans-isomer configuration.

68. The method of claim 67 in which $R_2$ is selected from a group consisting of:
  a dialkylaminoalkoxy group, and
  an alkyl sulfonyloxy alkoxy group.

69. The method of claim 68 wherein at least one of $R_1$ and $R_4$ is a methyl group.

70. The method of claim 69 wherein $R^1$ and $R_4$ are methyl groups.

71. The method of claim 70 wherein the $R_3$ is hydrogen.

72. The method of claim 71 wherein the $R_2$ group is in the para ring position.

73. The method of claim 67 in which $R_1$ is selected from a group consisting of:
  a dialkylaminoalkoxy group, and
  an alkylsulfonyloxy alkoxy group.

74. The method of claim 73 wherein at least one of $R^1$ and $R_4$ is a methyl group.

75. The method of claim 74 wherein $R^1$ and $R_4$ are methyl groups.

76. The method of claim 75 wherein the $R_2$ is hydrogen.

77. The method of claim 76 wherein the $R_3$ group is in the para ring position.

78. The method of claim 67 wherein the X is a chlorine atom.

79. A method of inhibiting the development of an estrogen-dependent tumor in a mammal in need of such therapy, comprising:
  administering to the mammal an effective amount of one or more of the compounds having the formula:

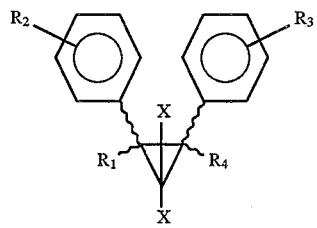

or any pharmaceutically acceptable salt thereof, in which:

X is a hydrogen or halogen atom;

$R_1$ is a hydrogen atom or a methyl group;

$R_2$ is selected from the group consisting of,
  a hydrogen atom, and
  a substituted alkoxy group in which the substituent of the alkoxy group is selected from a group consisting of,
    a dialkylamino group in which the alkyl substituent contains from 1 to 6 carbon atoms, and
    an alkylsulfonyloxy group in which the alkyl substituent contains from 1 to 6 carbon atoms;

$R_3$ is selected from the group consisting of,
  a hydrogen atom, and
  a substituted alkoxy group in which the substituent of the alkoxy group is selected from a group consisting of,
    a dialkylamino group in which the alkyl substituent contains from 1 to 6 carbon atoms, and
    an alkylsulfonyloxy group in which the alkyl substituent contains from 1 to 6 carbon atoms; and $R_4$ is a hydrogen atom or a methyl group; and with the proviso that $R_1$ and $R_1$ cannot simultaneously be hydrogen, and further with the proviso that $R_2$ and $R_3$ cannot simultaneously be hydrogen and wherein the bonds designated by ($\sim$)

represent that the compound can be in the cis- or trans-isomer configuration.

80. The method of claim 79 in which $R_2$ is selected from a group consisting of:
  a dialkylaminoalkoxy group, and
  an alkylsulfonyloxy alkoxy group.

81. The method of claim 80 wherein $R^1$ and $R_4$ are methyl groups.

82. The method of claim 81 wherein the $R_3$ is hydrogen.

83. The method of claim 82 wherein the $R_2$ group is in the para ring position.

84. The method of claim 79 in which $R_3$ is selected from a group consisting of:
  a dialkylaminoalkoxy group, and
  an alkylsulfonyloxy alkoxy group.

85. The method of claim 84 wherein $R_1$ and $R_4$ are methyl groups.

86. The method of claim 85 wherein the $R_2$ is hydrogen.

87. The method of claim 86 wherein the $R_3$ group is in the para ring position.

88. The method of claim 79 wherein the X is a chlorine atom.

* * * * *